(12) United States Patent
Smith

(10) Patent No.: US 10,000,750 B2
(45) Date of Patent: Jun. 19, 2018

(54) METHOD OF ISOLATING NUCLEIC ACID

(71) Applicant: PROMEGA CORPORATION, Madison, WI (US)

(72) Inventor: Donald B. Smith, Evansville, WI (US)

(73) Assignee: PROMEGA CORPORATION, Madison, WI (US)

( * ) Notice: Subject to any disclaimer, the term of this patent is extended or adjusted under 35 U.S.C. 154(b) by 306 days.

(21) Appl. No.: 14/879,429

(22) Filed: Oct. 9, 2015

(65) Prior Publication Data

US 2016/0102303 A1    Apr. 14, 2016

Related U.S. Application Data

(60) Provisional application No. 62/061,969, filed on Oct. 9, 2014.

(51) Int. Cl.
*C12N 15/10*  (2006.01)
*C12N 15/113*  (2010.01)

(52) U.S. Cl.
CPC ..... *C12N 15/1006* (2013.01); *C12N 15/1013* (2013.01); *C12N 15/113* (2013.01); *C12N 2310/14* (2013.01); *C12N 2310/141* (2013.01)

(58) Field of Classification Search
None
See application file for complete search history.

(56) References Cited

U.S. PATENT DOCUMENTS

| | | | |
|---|---|---|---|
| 5,981,235 A | 11/1999 | Shultz et al. | |
| 6,177,278 B1 | 1/2001 | Haj-Ahmad | |
| 6,291,248 B1 | 9/2001 | Haj-Ahmad | |
| 6,310,199 B1 | 10/2001 | Smith et al. | |
| 6,673,631 B1 | 1/2004 | Tereba et al. | |
| 7,989,614 B2 | 8/2011 | Deggerdal et al. | |
| 8,404,439 B2 | 3/2013 | Conrad | |
| 2013/0130917 A1 | 5/2013 | Cai | |
| 2016/0102303 A1 | 4/2016 | Smith | |

FOREIGN PATENT DOCUMENTS

| | | |
|---|---|---|
| EP | 2298891 | 9/2013 |
| EP | 1651761 | 9/2014 |

OTHER PUBLICATIONS

International Search Report for Application No. PCT/US2015/054878 dated Jan. 13, 2016 (9 pages).
Norgen Biotek(Canada) "microRNA Purification Kit (Cat. 21300)," Available online as early as 2016 <https://norgenbiotek.com/product/microrna-purification-kit>.
Qiagen, "miRNeasy Mini Kit," Available online as early as 2016, <https://www.qiagen.com/us/shop/sample-technologies/rna/mirneasy-mini-kit/#orderinginformation>.
Thermofisher, "mirVana™ miRNA kit, with phenol", Available online as early as 2015 <https://www.thermofisher.com/order/catalog/product/AM1560#/AM1560>.
Domnich et al. "Boron Carbide: Structure, Properties, and Stability under Stress," J. Am. Ceram. Soc., 94 [11] 3605-3628 (2011).

*Primary Examiner* — David C Thomas
(74) *Attorney, Agent, or Firm* — Michael Best & Friedrich LLP

(57) ABSTRACT

Disclosed herein is a method for isolating a nucleic acid from a sample. The method includes contacting the sample with boron carbide under conditions sufficient to form a boron carbide-nucleic acid complex. The complex is separated from the sample.

32 Claims, 7 Drawing Sheets

METHOD OF ISOLATING NUCLEIC ACID

CROSS REFERENCE TO RELATED APPLICATIONS

This application claims priority to U.S. Provisional Application No. 62/061,969 filed Oct. 9, 2014, which is incorporated herein by reference in its entirety.

TECHNICAL FIELD

The present invention relates to the isolation of nucleic acids.

BACKGROUND

Biological molecules (e.g., proteins and nucleic acids) are widely present in any number of materials such as tissue and cells, and often need to be isolated from the material to facilitate downstream detection or use of the biological molecule. Nucleic acid, for instance, is typically isolated using silica-based fixed bed columns or silica magnetic particles. Such silica-based methods, however, exclude nucleic acids that are smaller than about 200 nucleotides in length, for example, microRNAs (miRNAs), which have a length of about 21 nucleotides to about 26 nucleotides.

Accordingly, silica-based methods are combined with acid phenol and chloroform extraction (in the presence of high molarity guanidine isocyanate) to isolate both larger and smaller RNA molecules (e.g., total RNA). Acid phenol and chloroform extraction thus adds additional time and expense to the isolation of miRNAs, in addition to necessitating proper disposal of the organic waste material.

Accordingly, a need exists for the identification and development of new methods for the isolation of nucleic acids, especially miRNAs, to facilitate downstream detection and use of these isolated nucleic acids.

SUMMARY

The present invention is directed to a method for isolating a nucleic acid from a sample. The method comprises contacting the sample with a boron carbide composition under conditions sufficient to form a boron carbide-nucleic acid complex. The method also comprises separating the complex from the sample and eluting the nucleic acids from the complex, thereby isolating the nucleic acids.

The sample may be prepared in the absence of an organic extraction. The organic extraction may comprise phenol and chloroform. The phenol may be an acid phenol.

The method may further comprise contacting the sample with a chaotrope. The chaotrope may be present in a lysis or binding buffer. The chaotrope may be guanidine thiocyanate (GTC) or guanidine hydrochloride (GHCl).

The boron carbide composition may further comprise glass fibers.

The boron carbide-nucleic acid complex may be formed in the presence of an alcohol. The alcohol may be isopropanol or ethanol. Formation of the boron carbide-nucleic acid complex may comprise selective binding of the nucleic acid to the boron carbide. Selective binding may be dependent upon a concentration of an alcohol. The alcohol may be isopropanol or ethanol.

The nucleic acid may be RNA. The RNA may selectively bind the boron carbide when the concentration of alcohol is from about 15% v/v to about 100% v/v.

The RNA may be large RNA. The large RNA may selectively bind the boron carbide when the concentration of isopropanol is from about 15% to about 20%.

The RNA may be large RNA. The large RNA may selectively bind the boron carbide when the concentration of ethanol is from about 20% v/v to about 35% v/v.

The RNA may be small RNA. The small RNA may selectively bind the boron carbide when the concentration of isopropanol is about 40% v/v to about 60% v/v.

The RNA may be small RNA. The small RNA may selectively bind the boron carbide when the concentration of ethanol is about 50% v/v to about 70% v/v.

The RNA may be long, noncoding RNA. The small RNA may be selected from the group consisting of microRNA (miRNA), small interfering RNA (siRNA), piwi-interacting RNA (piRNA), small noncoding RNA, small nuclear RNA (snRNA), small nucleolar RNA (snoRNA), and transfer RNA (tRNA). The small RNA may be miRNA.

The nucleic acid may be RNA. The RNA may be small RNA. The RNA may be microRNA (miRNA). The RNA may comprise RNA molecules having a length of about 5 nucleotides to about 200 nucleotides. The RNA may comprise RNA molecules having a length of about 10 nucleotides to about 100 nucleotides. The RNA may comprise RNA molecules having a length of about 18 nucleotides to about 30 nucleotides.

The boron carbide may have a particle size of about 1 micron to about 20 microns. The boron carbide particles may be in a suspension. The boron carbide may be associated with a solid support. The solid support may be selected from the group consisting of a magnetic particle and a column. The solid support may be used in a magnetic, centrifugation, or filtration format.

The method may further comprise using or characterizing the isolated nucleic acid.

DETAILED DESCRIPTION

Figure 1:
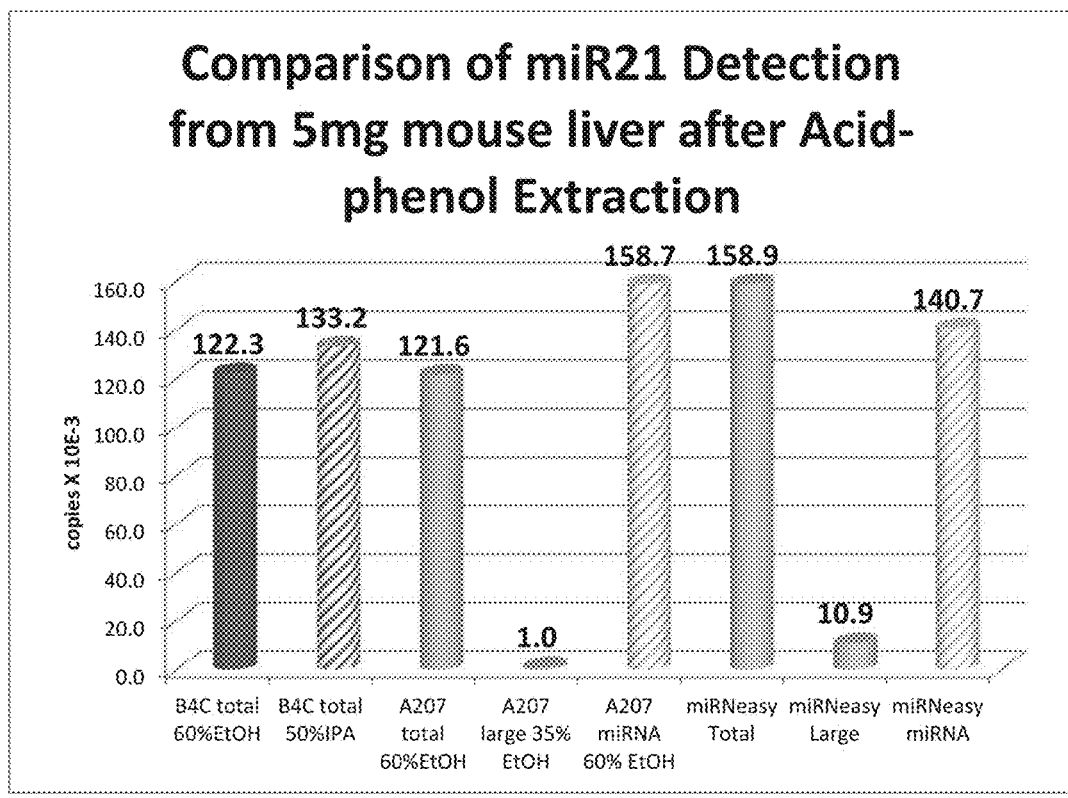
FIG. 1 shows detection of miR21 from RNA isolated using acid phenol and chloroform extraction in combination with each of boron carbide, A207, and miRNeasy.

The present invention relates to a method for isolating a biological molecule from a sample. The method includes contacting the sample with a boron carbide composition under conditions sufficient to form a boron carbide-biological molecule complex. When the biological molecule is a nucleic acid, formation of a boron carbide-nucleic acid complex may be dependent on a concentration of an alcohol (e.g., ethanol or isopropanol). For example, RNA binds boron carbide in the presence of concentrations of isopropanol greater than 15% v/v isopropanol. Additionally, the concentration of isopropanol may be used to discriminate between large and small RNAs, e.g., boron carbide is bound by large and small RNAs in presence of about 15% v/v to about 26% v/v isopropanol and about 40% v/v to about 70% v/v isopropanol, respectively.

This differential binding of RNA to boron carbide allows the method of the invention to discriminate between different sizes of RNA simply based upon alcohol concentration. This differential binding, in turn, allows for the sequential isolation of different sizes and/or types of RNA from a single sample. The sample may be contacted one or more times with boron carbide, in which each time, the concentration of alcohol is adjusted depending on the type and size of nucleic acid to be isolated from the sample.

The method further allows for the isolation of small RNAs, for example, miRNAs. miRNA isolation is not dependent on acid phenol/chloroform/guanidine isocyanate extraction prior to contacting the sample with boron carbide. Rather, the method yields similar quantities of small RNA alone or in combination with acid phenol/chloroform/guanidine isocyanate extraction. Therefore, the present invention provides an advantage in being compatible with applications that require acid phenol/chloroform/guanidine isocyanate extraction, yet when not required, time and expense may be saved by foregoing the acid phenol/chloroform/guanidine isocyanate extraction.

1. DEFINITIONS

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present invention. All publications, patent applications, patents and other references mentioned herein are incorporated by reference in their entirety. The materials, methods, and examples disclosed herein are illustrative only and not intended to be limiting.

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "and" and "the" include plural references unless the context clearly dictates otherwise. The present disclosure also contemplates other embodiments "comprising," "consisting of" and "consisting essentially of," the embodiments or elements presented herein, whether explicitly set forth or not.

The term "magnetic," as used herein, refers to a solid support capable of having a magnetic moment imparted to it when placed in a magnetic field, and thus is displaceable under the action of that field.

The term "sample," as used herein, generally refers to any material containing nucleic acid, including for example, foods and allied products, clinical, and environmental samples. However, the sample will generally be a biological sample, which may contain any viral or cellular material, including all prokaryotic or eukaryotic cells, viruses, bacteriophages, mycoplasmas, protoplasts, and organelles. Such biological material may thus comprise all types of mammalian and non-mammalian animal cells, plant cells, algae including blue-green algae, fungi, bacteria, protozoa, etc. Representative samples thus include whole blood and blood-derived products such as plasma, serum and buffy coat, urine, feces, cerebrospinal fluid or any other body fluids, tissues, cell cultures, cell suspensions, etc. The sample may comprise a lysate. The sample may also include relatively pure starting material such as a PCR product, or semi-pure preparations obtained by other nucleic acid recovery processes.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9, and 7.0 are explicitly contemplated.

2. METHOD OF ISOLATION

The present invention relates to a method for isolating a biological molecule from a sample. The biological molecule may be a nucleic acid. The method includes contacting the sample with a boron carbide composition under conditions sufficient to form a boron carbide-biological molecule complex. The boron carbide-biological molecule complex may be formed in the presence of one or more alcohols. The alcohol may be ethanol or isopropanol. In particular, the alcohol may facilitate or drive binding of the biological molecule to the boron carbide such that formation of the boron carbide-biological molecule complex is dependent upon a concentration of the alcohol. Accordingly, the method advantageously provides a user control over the interaction between the biological molecule and the boron carbide.

The method also includes separating the boron carbide-biological molecule complex from the sample. The method may further include washing the boron carbide-biological molecule complex prior to selectively removing the biological molecule from the complex. Selectively removing the biological molecule from the complex may include eluting the biological molecule from the complex. Eluting the biological molecule from the complex may include disrupting the interaction between the biological molecule and the boron carbide, thereby yielding the isolated biological molecule.

The method may further include contacting the sample with the boron carbide composition under conditions sufficient to form a second boron carbide-biological molecule complex. The second boron carbide-biological molecule complex may be separated from the sample. The biological molecules of the first and second complexes may be the same or different.

In some embodiments, if the biological molecules in the first and second complexes are the same (or if different, of a certain size range, e.g., small RNAs), the sample may be contacted with the boron carbide composition to form the first complex. Upon separation of the first complex from the sample, the sample may again be contacted with the boron carbide composition to form the second complex, thereby capturing any biological molecule that was not captured within the first complex. This may be done iteratively, in a sequential fashion, forming the first complex, the second complex, the third complex, and so forth (up to $n^{th}$ complexes), in which each subsequent complex captures any biological molecule not captured by the prior complex, thereby increasing the amount of the biological molecule isolated from the sample.

In other embodiments, if the biological molecules in the first and second complexes are the same, but of different sizes (e.g., different polymer lengths, molecular weights, etc.), the first and second biological molecules may bind boron carbide in the presence of different concentrations of alcohol. In other words, at a concentration of x % v/v alcohol, the first biological molecule, but not the second biological molecule, may bind boron carbide. At a second concentration of y % v/v alcohol, the second biological molecule, but not the first biological molecule, may bind boron carbide. Accordingly, the first and second complexes are formed in the presence of different concentrations (i.e., x % v/v and y % v/v, respectively) of alcohol, thereby allowing for the isolation of different sizes of the biological molecule from the sample. Such isolation may be sequential.

If the biological molecules in the first and second complexes are different from one another, the first and second biological molecules may bind boron carbide in the presence of different concentrations of alcohol. In other words, at a concentration of x % v/v alcohol, the first biological molecule, but not the second biological molecule, may bind boron carbide. At a second concentration of y % v/v alcohol, the second biological molecule, but not the first biological molecule, may bind boron carbide. Accordingly, the first and second complexes are formed in the presence of different concentrations (i.e., x % v/v and y % v/v, respectively) of alcohol, thereby allowing for the isolation of more than one biological molecule from the sample. Such isolation may be sequential.

The method may further comprise using or characterizing the isolated biological molecule as described in more detail below.

a. Boron Carbide Composition

The method includes contacting the sample with the boron carbide composition to form the boron carbide-biological molecule complex. The boron carbide composition may further comprise glass fibers as described below. Boron carbide exhibits a complex structure, which includes a mixture of carbon-boron-carbon (C—B—C) chains and boron icosahedra ($B_{12}$). Within this structure, boron is able to interact with the biological molecule. This interaction between boron and the biological molecule is facilitated by alcohol. As discussed below, the alcohol may be, but is not limited to, ethanol, isopropanol, or a combination thereof.

The boron carbide may be in the form of a particle. The particle may be a micro grit, in which the particle has a size of about 1 micron to about 53 microns. The boron carbide may have a particle size of about 1 micron to about 45 microns, about 1 micron to about 20 microns or about 3 microns to about 15 microns. The particle size of boron carbide may be about 1 micron, about 2 microns, about 3 microns, about 4 microns, about 5 microns, about 6 microns, about 7 microns, about 8 microns, about 9 microns, about 10 microns, about 11 microns, about 12 microns, about 13 microns, about 14 microns, about 15 microns, about 16 microns, about 17 microns, about 18 microns, about 19 microns, about 20 microns, about 21 microns, about 22 microns, about 23 microns, about 24 microns, about 25 microns, about 26 microns, about 27 microns, about 28 microns, about 29 microns, about 30 microns, about 31 microns, about 32 microns, about 33 microns, about 34 microns, about 35 microns, about 36 microns, about 37 microns, about 38 microns, about 39 microns, about 40 microns, about 41 microns, about 42 microns, about 43 microns, about 44 microns, or about 45 microns. The particle size of boron carbide may also be about 4 microns or about 13 microns.

The boron carbide particles may be in a liquid suspension (e.g., slurry) or a packed state. The boron carbide may be associated with a solid support (e.g., a column or magnetic particle). The boron carbide may be in a mixture with other materials, for example, glass fiber, which may then be associated with the solid support.

(1) Glass Fiber

The boron carbide composition may further include glass fibers. The glass fibers and boron carbide may form a matrix. This matrix may provide an improved flow rate when the boron carbide is associated with a solid support such as a column as described below. The matrix may also provide increased capacity for binding of the biological molecule because the glass fibers may also have an affinity for the biological molecule, and thus, contribute to binding of the biological molecule. Accordingly, the matrix may improve the efficiency of binding the biological molecule.

(2) Solid Support

The boron carbide may be associated with the solid support, for example, but not limited to, a column and a magnetic particle. The solid support may be used in, but is not limited to, a magnetic format, a centrifugation format, a filtration format, or any combination thereof.

(a) Column

Boron carbide may be associated with a solid support such as a column. In particular, boron carbide particles may be packed and retained in the column. The boron carbide particles may be packed together with another material, for example, glass fiber, to maintain a consistent flow rate through the column. The glass fiber may not substantially impact the formation of the boron carbide-biological molecule complex. Accordingly, as the sample is passed through the column, boron carbide contacts the sample and forms the boron carbide-biological molecule complex. Because boron carbide is retained within the column, the boron carbide-biological molecule complex is separated from the sample once the sample has completely flowed through the column.

(b) Magnetic Particle

The boron carbide may be associated with a solid support such as a magnetic or superparamagnetic particle. The particle may be coated with the boron carbide, e.g., by depositing a layer of boron carbide. Accordingly, the magnetic particle may be added to the sample for a period of time sufficient to allow for the formation of the boron carbide-biological molecule complex. The magnetic particle, along with the boron carbide-biological molecule complex, may be removed onto a suitable surface, and thus separated from the sample, by the application of a magnetic field (e.g., using a permanent magnet). It is usually sufficient to apply the magnet to the side of a vessel containing the sample to aggregate the particles to a wall of the vessel and to pour away (or otherwise remove) the remainder of the sample. Accordingly, magnetic particles coated with boron carbide may be readily removed from the sample by magnetic aggregation, which provides a quick, simple, and efficient way of separating the boron carbide-biological molecule complex from the sample.

b. Alcohol

Formation of the boron carbide-biological molecule complex may occur in the presence of one or more alcohols, for example, but not limited to, ethanol and isopropanol. The alcohol may facilitate or drive binding of the biological molecule to the boron carbide such that formation of the boron-carbide-biological molecule complex is dependent on the concentration of the alcohol.

(1) Isopropanol

Formation of the boron carbide-biological molecule complex may occur in the presence of isopropanol (i.e., also known as 2-propanol, sec-propyl alcohol, and isopropyl alcohol). The isopropanol may facilitate or drive binding of the biological molecule to the boron carbide such that formation of the boron carbide-biological molecule complex is dependent on the concentration of isopropanol.

When the biological molecule is a nucleic acid, such as RNA as described below in more detail, the isopropanol may facilitate the interaction between the boron carbide and the nucleic acid. The isopropanol concentration may determine whether large RNA, small RNA, or a combination thereof binds the boron carbide. Accordingly, the method described herein may employ any number of isopropanol concentrations to allow the user to determine which kind and size of nucleic acid binds boron carbide to form a respective boron carbide-nucleic acid complex.

Boron carbide may bind RNA at a concentration of about 15% isopropanol to about 70% isopropanol. Boron carbide may bind RNA at a concentration of about 15% v/v, 16% v/v, 17% v/v, 18% v/v, 19% v/v, 20% v/v, 21% v/v, 22% v/v, 23% v/v, 24% v/v, 25% v/v, 26% v/v, 27% v/v, 28% v/v, 29% v/v, 30% v/v, 31% v/v, 32% v/v, 33% v/v, 34% v/v, 35% v/v, 36% v/v, 37% v/v, 38% v/v, 39% v/v, 40% v/v, 41% v/v, 42% v/v, 43% v/v, 44% v/v, 45% v/v, 46% v/v, 47% v/v, 48% v/v, 49% v/v, 50% v/v, 51% v/v, 52% v/v, 53% v/v, 54% v/v, 55% v/v, 56% v/v, 57% v/v, 58% v/v, 59% v/v, 60% v/v, 61% v/v, 62% v/v, 63% v/v, 64% v/v, 65% v/v, 66% v/v, 67% v/v, 68% v/v, 69% v/v, or 70% v/v isopropanol.

Boron carbide may bind large RNAs (as described below) in the presence of about 15% v/v isopropanol to about 30% v/v isopropanol, about 15% v/v isopropanol to about 20% v/v isopropanol, or about 15% v/v isopropanol, about 16% v/v isopropanol, about 17% v/v isopropanol, about 18% v/v isopropanol, about 19% v/v isopropanol, about 20% v/v isopropanol, about 21% v/v isopropanol, about 22% v/v isopropanol, about 23% v/v isopropanol, about 24% v/v isopropanol, about 25% v/v isopropanol, about 26% v/v isopropanol, about 27% v/v isopropanol, about 28% v/v isopropanol, about 29% v/v isopropanol, or about 30% v/v isopropanol.

In some embodiments, about 15% v/v isopropanol to about 26% v/v isopropanol may provide greater selectivity for binding of the large RNAs to boron carbide as compared to concentrations of isopropanol that are less than about 15% v/v or greater than about 26% v/v. In other embodiments, boron carbide may bind large RNAs at concentrations greater than about 26% v/v isopropanol, but with less (or reduced) selectivity for the large RNAs as compared to about 15% v/v isopropanol to about 26% v/v isopropanol.

Boron carbide may bind small RNAs (as described below) in presence of about 40% v/v isopropanol to about 70% v/v isopropanol, about 40% v/v isopropanol to about 65% v/v isopropanol, about 40% v/v isopropanol to about 60% v/v isopropanol, or about 40% v/v isopropanol to about 55% v/v isopropanol. Boron carbide may bind small RNAs in the presence of about 40% v/v, 41% v/v, 42% v/v, 43% v/v, 44% v/v, 45% v/v, 46% v/v, 47% v/v, 48% v/v, 49% v/v, 50% v/v, 51% v/v, 52% v/v, 53% v/v, 54% v/v, 55% v/v, 56% v/v, 57% v/v, 58% v/v, 59% v/v, 60% v/v, 61% v/v, 62% v/v, 63% v/v, 64% v/v, 65% v/v, 66% v/v, 67% v/v, 68% v/v, 69% v/v, or 70% v/v isopropanol.

In some embodiments, boron carbide may bind small RNAs in presence of less than about 40% v/v isopropanol (e.g., about 25% v/v isopropanol). In other embodiments, boron carbide may bind small RNAs in the presence of less than 40% v/v isopropanol and acidic conditions.

(2) Ethanol

Formation of the boron carbide-biological molecule complex may occur in the presence of ethanol. Ethanol may facilitate or drive binding of the biological molecule to the boron carbide such that formation of the boron carbide-biological molecule complex is dependent on the concentration of ethanol.

Boron carbide may bind large RNAs (described below) in the presence of about 20% v/v ethanol to about 35% v/v ethanol, or about 20% v/v ethanol, about 21% v/v ethanol, about 22% v/v ethanol, about 23% v/v ethanol, about 24% v/v ethanol, about 25% v/v ethanol, about 26% v/v ethanol, about 27% v/v ethanol, about 28% v/v ethanol, about 29% v/v ethanol, about 30% v/v ethanol, about 31% v/v ethanol, about 32% v/v ethanol, about 33% v/v ethanol, about 34% v/v ethanol, or about 35% v/v ethanol.

Boron carbide may bind small RNAs (described below) in the presence of about 50% v/v ethanol. Boron carbide may also bind small RNAs in the presence of about 50% v/v ethanol to about 70% v/v ethanol, or greater than about 50% v/v ethanol, greater than about 55% v/v ethanol, greater than about 60% v/v ethanol, greater than about 65% v/v ethanol, greater than about 70% v/v ethanol, or greater than about 75% v/v ethanol.

c. Biological Molecule (1) Nucleic Acid

As described above, the method may isolate the biological molecule from the sample by contacting the sample with boron carbide to form the boron carbide-biological molecule complex. Formation of the complex by facilitated by one or more alcohols (e.g., ethanol or isopropanol) as described above. The complex may then be separated from the sample and the biological molecule is removed from the complex to yield the isolated biological molecule. The biological molecule may be a nucleic acid or a derivative thereof. The nucleic acid may RNA as described below in more detail.

(a) RNA

Boron carbide may bind RNA or a derivative thereof. Boron carbide is capable of binding small RNAs, large RNAs, or a combination thereof. The interaction between boron carbide and RNA may occur in the presence of one or more alcohols, for example, isopropanol or ethanol as described above.

(a) Large RNA

The RNA that binds boron carbide may be a large RNA. The large RNA may be a messenger RNA (mRNA), a ribosomal RNA (rRNA), a large noncoding RNA, a large intergenic noncoding RNA, a small nucleolar RNA (snoRNA), or a small nuclear RNA (snRNA). The large RNA may be RNA generated in vitro, for example, transcribed RNA. The large RNA may be modified or labeled (e.g., biotin, FITC). The large RNA may be enzymatically modified, for example, by the addition of a radiolabel (e.g., $^{32}P$).

The large RNA may have a length greater than about 200 nucleotides, greater than about 250 nucleotides, greater than about 300 nucleotides, greater than about 350 nucleotides, greater than about 400 nucleotides, greater than about 450 nucleotides, greater than about 500 nucleotides, greater than about 600 nucleotides, greater than about 700 nucleotides, greater than about 800 nucleotides, greater than about 900 nucleotides, greater than about 1000 nucleotides, greater than about 1500 nucleotides, greater than about 2000 nucleotides, or greater than about 2500 nucleotides.

(b) Small RNA

The RNA that binds boron carbide may be a small RNA. The small RNA may be a small noncoding RNA. The small noncoding RNA may be a transfer RNA (tRNA), a small noncoding RNA, a microRNA (miRNA), a miRNA precursor (pre-miRNA), a small interfering RNA (siRNA), a snRNA, a snoRNA, a piwi interacting RNA (piRNA), or an mRNA. The small RNA may be a miRNA. The small RNA may be RNA generated in vitro, for example, transcribed or chemically synthesized RNA. The chemically synthesized RNA may be a RNA oligomer (oligo) and may be modified or labeled (e.g., biotin, FITC). The small RNA may be enzymatically modified, for example, by the addition of a radiolabel (e.g., $^{32}P$).

The small RNA may have a length of about 5 nucleotides to about 200 nucleotides, about 5 nucleotides to about 150 nucleotides, about 5 nucleotides to about 100 nucleotides, about 5 nucleotides to about 50 nucleotides, about 5 nucleotides to about 30 nucleotides. The small RNA may also have a length of about 10 nucleotides to about 200 nucleotides, about 10 nucleotides to about 150 nucleotides, about 10 nucleotides to about 100 nucleotides, about 10 nucleotides to about 50 nucleotides, or about 10 nucleotides to about 30 nucleotides. The small RNA may have a length of about 18 nucleotides to about 30 nucleotides, about 18 nucleotides to about 25 nucleotides, or about 18 nucleotides to about 21 nucleotides. The small RNA may also have a length of about 5 nucleotides, about 6 nucleotides, about 7 nucleotides, about 8 nucleotides, about 9 nucleotides, about 10 nucleotides, about 11 nucleotides, about 12 nucleotides, about 13 nucleotides, about 14 nucleotides, about 15 nucleotides, about 16 nucleotides, about 17 nucleotides, about 18 nucleotides, about 19 nucleotides, about 20 nucleotides, about 21 nucleotides, about 22 nucleotides, about 23 nucleotides, about 24 nucleotides, about 25 nucleotides, about 26 nucleotides, about 27 nucleotides, about 28 nucleotides, about 29 nucleotides, or about 30 nucleotides.

d. Sample Treatment Prior to Formation of the Boron Carbide-Biological Molecule Complex The biological molecule may be isolated from the sample by contacting the sample with the boron carbide to form the boron carbide-biological molecule complex. Optionally, the sample may be treated prior to the addition of boron carbide to the sample. Such treatment may include, but is not limited to, dilution, ultrafiltration, extraction, precipitation, dialysis, enzymatic digestion, and homogenization. Moreover, if such treatment methods are employed with the sample, such treatment methods have biological molecule that remains in the sample at a concentration proportional to that in an untreated sample (e.g., namely, a sample that is not subjected to any such treatment method(s)).

For instance, if the sample is a tissue and/or cell(s), the sample may be homogenized to disrupt the tissue and/or cell(s) and generate a lysate. Homogenization releases the biological molecule from association with other material in the tissue and/or cell(s) so that the biological molecule may form the complex with boron carbide.

Homogenization may occur in the presence or absence of an organic solvent such as acid phenol and chloroform. The acid phenol and chloroform in combination with high molarity guanidine isocyanate may be used to extract RNA, including small RNAs, from associated proteins. The extracted RNA is soluble in the aqueous phase and able to bind boron carbide in the presence of one or more alcohols (e.g., isopropanol or ethanol). If homogenization occurs in the absence of the organic solvent (e.g., acid phenol and chloroform), boron carbide is still able to bind RNA, including small RNAs such as miRNAs, in the lysate. Accordingly, boron carbide as used in the method described herein advantageously allows for the isolation of small RNAs regardless of whether the sample is homogenized in the presence or absence of the organic solvent (e.g., acid phenol and chloroform).

In other embodiments, if the sample is a tissue and/or cells, the sample may be treated or contacted with a lysis solution to form a lysate. Such a lysis solution may include one or more chaotropes, for example, but not limited to, a guanidinium salt (e.g., guanidine thiocyanate (GTC) and guanidine hydrochloride (HCl)).

e. Formation of the Boron Carbide-Biological Molecule Complex

The sample is contacted with boron carbide under conditions sufficient to form the boron carbide-biological molecule complex. Such conditions may include a binding solution; the binding solution (as described below), may include the alcohol described above. In other embodiments, such conditions may not include the binding solution, but may include the alcohol described above.

The alcohol (e.g., ethanol or isopropanol) may facilitate the binding of the biological molecule to the boron carbide, and thus, the alcohol may facilitate or promote formation of the boron carbide-biological molecule complex. Additionally, the formation of the boron carbide-biological molecule complex may be dependent on the concentration of the alcohol, thereby allowing the user to control formation of the complex via alcohol concentration.

The isopropanol concentration may be used to segregate large and small RNAs. As described above, large RNAs may bind boron carbide in the presence of about 15% v/v to about 30% v/v isopropanol while small RNAs may bind boron carbide at concentrations of isopropanol of about 40% v/v to about 70% v/v. In another example (and also as described above), ethanol concentration may be used to segregate large and small RNAs. In the presence of about 20% v/v to about 35% v/v ethanol, boron carbide may bind large RNAs, while in the presence of greater than about 50% v/v ethanol (or about 50% v/v ethanol), boron carbide may bind small RNAs.

The boron carbide-biological molecule complex may be a first complex. Accordingly, the sample may be further contacted with boron carbide under conditions sufficient to form the second boron carbide-biological molecule complex. Such conditions may include the binding solution. The binding solution (as described below), may include the alcohol described above. In other embodiments, such conditions may not include the binding solution, but may include the alcohol described above.

For instance, the biological molecule in the first complex (i.e., first biological molecule) may be large RNA while the biological molecule in the second complex (i.e., second biological molecule) may be small RNA. As described above, large RNA binds boron carbide at lower concentrations of isopropanol or ethanol than small RNAs. Accordingly, the sample may first be contacted with boron carbide in the presence of a first concentration of isopropanol or ethanol to form the boron carbide-large RNA complex. The boron carbide-large RNA complex may then be separated from the sample.

The sample may again be contacted with boron carbide, but now in the presence of a second concentration of isopropanol or ethanol (which is higher than the first concentration) to form the boron carbide-small RNA complex. The boron carbide-small RNA complex may then be separated from the sample.

Accordingly, as illustrated in this non-limiting example, the combination of boron carbide and isopropanol or ethanol concentration provide the advantageous property of allowing isolation of more than one biological molecule from the sample. This combination of boron carbide and isopropanol or ethanol concentration may be used to isolate any number of biological molecules from the sample as long as each biological molecule(s) binds boron carbide at a discrete or distinguishable concentration of isopropanol or ethanol.

In another example, the biological molecules in the first and second complexes may be the same (or if different, of a certain size range, e.g., small RNAs). As such, the sample may be contacted with the boron carbide composition to form the first complex. Upon separation of the first complex from the sample, the sample may again be contacted with the boron carbide composition to form the second complex, thereby capturing any biological molecule that was not captured within the first complex. This may be done iteratively, in a sequential fashion, forming the first complex, the second complex, the third complex, and so forth (up to $n^{th}$ complexes), in which each subsequent complex captures any biological molecule not captured by the prior complex, thereby increasing the amount of the biological molecule isolated from the sample.

(1) Binding Solution

As described above, the sample may be contacted with the boron carbide composition in the presence of the binding solution. The binding solution may include, but is not limited to, a guanindinium salt and the alcohol (e.g., isopropanol or ethanol) described above. The guanindinium salt may be, but is not limited to, guanidine thiocyanate (GTC), guanidine hydrochloride (GHCl), and the combination thereof.

In some embodiments, the binding solution may further include a buffer. The buffer may include, but is not limited to, sodium citrate, sodium acetate, and the combination thereof. The buffer may be present in the binding solution at sufficient ionic strength to overcome the biological pH of the sample. The buffer may be present in the binding solution at a concentration of about 0.05 M to about 0.1 M or about 0.05 M, 0.06 M, 0.07 M, 0.08 M, 0.09 M, or 0.1 M. The buffer may have a pH of about 4.0 to about 5.0 or about 4.0, 4.1, 4.2, 4.3, 4.4, 4.5, 4.6, 4.7, 4.8, 4.9, or 5.0.

f. Washing of the Boron Carbide-Biological Molecule Complex

Once the boron carbide-biological molecule complex is formed, the complex may be separated from the sample, for example, by use of the solid support described above. The separated complex may further be optionally washed to remove one or more contaminants without disruption of the boron carbide-biological complex. Washing may include incubating the complex with a wash solution. Such incubation may occur for about 1 second to about 15 minutes, about 1 second to about 10 minutes, about 1 second to about 5 minutes, about 1 second to about 1 minute, about 1 second to about 30 seconds, or about 1 second, about 5 seconds, about 10 seconds, about 15 seconds, about 20 seconds, about 25 seconds, about 30 seconds, about 35 seconds, about 40 seconds, about 45 seconds, about 50 seconds, about 55 seconds, about 60 seconds, about 70 seconds, about 80 seconds, about 90 seconds, about 100 seconds, about 110 seconds, about 120 seconds, about 3 minutes, about 4 minutes, about 5 minutes, about 6 minutes, about 7 minutes, about 8 minutes, about 9 minutes, about 10 minutes, about 11 minutes, about 12 minutes, about 13 minutes, about 14 minutes, or about 15 minutes.

The separated complex may further be subjected to any number of treatments to remove contaminants without disrupting the boron carbide-biological molecule complex. Such treatments include, but are not limited to, the addition of RNAse, DNAse, protease, or a combination thereof. When the biological molecule is a nucleic acid, the separated complex may be incubated with a protease (e.g., proteinase K) to digest any protein associated with the nucleic acid. Such digested protein may then be removed by washing the complex with the wash solution. In some embodiments, when the nucleic acid is RNA, the treatment may further (or instead) include incubating the boron carbide-RNA complex with DNAse to digest any DNA associated with the RNA or boron carbide. Such digested DNA may then be removed by washing the boron carbide-RNA complex with the wash solution.

(1) Wash Solution

The wash solution may be employed to wash the separated boron carbide-biological molecule complex. The wash solution may include, but is not limited to, one or more salts, one or more buffers, one or more alcohols, and any combination thereof.

The salt may be potassium acetate (KOAc). The salt may be present in the wash solution at a concentration of about 10 mM to about 150 mM, about 20 mM to about 100 mM, or about 30 mM to about 80 mM. The salt may be present in the wash solution at a concentration of about 10 mM, 15 mM, 20 mM, 25 mM, 30 mM, 35 mM, 40 mM, 45 mM, 50 mM, 55 mM, 60 mM, 65 mM, 70 mM, 75 mM, 80 mM, 85 mM, 90 mM, 95 mM, 100 mM, 105 mM, 110 mM, 115 mM, 120 mM, 125 mM, 130 mM, 135 mM, 140 mM, 145 mM, or 150 mM. The salt may be present in the wash solution at a concentration of about 60 mM. In some embodiments, the wash solution may include about 60 mM potassium acetate.

The buffer may be tris(hydroxymethyl)aminomethane (also known herein as "Tris"). The buffer may be present in the wash solution at a concentration of about 1 mM to about 50 mM, about 2 mM to about 30 mM, or about 5 mM to about 15 mM. The buffer may be present in the wash solution at a concentration of about 1 mM, 2 mM, 3 mM, 4 mM, 5 mM, 6 mM, 7 mM, 8 mM, 9 mM, 10 mM, 11 mM, 12 mM, 13 mM, 14 mM, 15 mM, 16 mM, 17 mM, 18 mM, 19 mM, 20 mM, 25 mM, 30 mM, 35 mM, 40 mM, 45 mM, or 50 mM. The buffer may be present in the wash solution at a concentration of about 10 mM. In some embodiments, the wash solution may include about 10 mM Tris.

The alcohol may be ethanol. The alcohol may be present in the wash solution at a concentration of about 40% v/v to about 80% v/v, about 45% v/v to about 75% v/v, or about 50% v/v to about 70% v/v. The alcohol may be present in the wash solution at a concentration of about 40% v/v, 41% v/v, 42% v/v, 43% v/v, 44% v/v, 45% v/v, 46% v/v, 47% v/v, 48% v/v, 49% v/v, 50% v/v, 51% v/v, 52% v/v, 53% v/v, 54% v/v, 55% v/v, 56% v/v, 57% v/v, 58% v/v, 59% v/v, 60% v/v, 61% v/v, 62% v/v, 63% v/v, 64% v/v, 65% v/v, 66% v/v, 67% v/v, 68% v/v, 69% v/v, 70% v/v, 71% v/v, 72% v/v, 73% v/v, 74% v/v, 75% v/v, 76% v/v, 77% v/v, 78% v/v, 79% v/v, or 80% v/v. The alcohol may be present in the wash solution at a concentration of about 60% v/v. In some embodiments, the wash solution may include about 60% v/v ethanol.

The wash solution may have a pH of about 6.0 to about 9.0, about 6.5 to about 8.5, or about 7.0 to about 8.0. The wash solution may have a pH of about 6.0, 6.1, 6.2, 6.3, 6.4, 6.5, 6.6, 6.7, 6.8, 6.9, 7.0, 7.1, 7.2, 7.3, 7.4, 7.5, 7.6, 7.7, 7.8, 7.9, 8.0, 8.1, 8.2, 8.3, 8.4, 8.5, 8.6, 8.7, 8.8, 8.9, or 9.0. The wash solution may have a pH of about 7.5.

In other embodiments, the wash solution may include 60 mM potassium acetate, 10 mM Tris, 60% v/v ethanol, and a pH of 7.5.

g. Separation of the Biological Molecule from Boron Carbide

The sample may be contacted with boron carbide to form the boron carbide-biological molecule complex. The complex may be separated from the sample. The separated complex may be optionally washed as described above. The biological molecule may be removed or separated from the complex to yield the isolated biological molecule. In particular, the complex may be incubated with an elution solution that disrupts the interaction between the boron carbide and the biological molecule. After incubation of the complex with the elution solution, the biological molecule is eluted from the complex.

(1) Elution Solution

The elution solution may be utilized to remove or separate the biological molecule from the complex to yield the isolated biological molecule. The elution solution, for example, may have a pH which is sufficiently high to disrupt the interaction between boron carbide and the biological molecule. The elution solution may be water.

In other embodiments, the elution solution may include a low ionic buffer. The low ionic buffer may contain, but is not limited to, Tris, ethylenediaminetetraacetic acid (also known herein as "EDTA"), and the combination thereof. In some embodiments, the low ionic buffer may include about 0.1 mM Tris to about 2.0 mM Tris and about 0.01 mM EDTA to about 1.0 mM EDTA. The low ionic buffer may include about 0.1 mM, 0.2 mM, 0.3 mM, 0.4 mM, 0.5 mM, 0.6 mM, 0.7 mM, 0.8 mM, 0.9 mM, 1.0 mM, 1.1 mM, 1.2 mM, 1.3 mM, 1.4 mM, 1.5 mM, 1.6 mM, 1.7 mM, 1.8 mM, 1.9 mM, or 2.0 mM Tris and about 0.01 mM, 0.02 mM, 0.03 mM, 0.04 mM, 0.05 mM, 0.06 mM, 0.07 mM, 0.08 mM, 0.09 mM, 0.1 mM, 0.2 mM, 0.3 mM, 0.4 mM, 0.5 mM, 0.6 mM, 0.7 mM, 0.8 mM, 0.9 mM, or 1.0 mM EDTA. The lower ionic buffer may have a pH of about 8.0 to about 9.0. The low ionic buffer may have a pH about 8.0, 8.1, 8.2, 8.3, 8.4, 8.5, 8.6, 8.7, 8.8, 8.9, or 9.0. In some embodiments, the low ionic buffer may include about 1 mM Tris and about 0.1 mM EDTA and have a pH of about 8.5.

h. Use or Characterization of the Isolated Biological Molecule

The isolated biological molecule can be used or characterized in any number of assays known to one of skill in the art. When the biological molecules is a nucleic acid, such assays may include, but are not limited to, reverse transcriptase polymerase chain reaction (RT-PCR), quantitative or real-time PCR (qPCR), hybridization assay (e.g., Northern blotting), and spectrometric assay (e.g., absorbance at 260 and 280 nanometers).

3. KIT

Provided herein is a kit that can be utilized in the method described above to isolate the biological molecule from the sample. The kit may include one or more containers for holding the solutions and/or boron carbide described in the method. The kit may also include other material(s), which may be desirable from a user standpoint, such as a buffer(s), a diluent(s), a standard(s), and/or other material useful in sample processing, washing, or conducting any other step of the method described herein.

The kit according to the present disclosure preferably includes instructions for carrying out the method of the invention. Instructions included in the kit of the present disclosure may be affixed to packaging material or may be included as a package insert. While instructions are typically written or printed materials, they are not limited to such. Any medium capable of storing such instructions and communicating them to an end user is contemplated by this disclosure. Such media include, but are not limited to, electronic storage media (e.g., magnetic discs, tapes, cartridges, chips), optical media (e.g., CD ROM), and the like. As used herein, the term "instructions" can include the address of an internet site which provides instructions.

The present invention has multiple aspects, illustrated by the following non-limiting examples.

4. EXAMPLES

Example 1

Materials and Methods for Example 2

Method for RNA Isolation with Boron Carbide and Acid Phenol/Chloroform.

Tissue was homogenized for 30 seconds at moderate speed using 700 μl Trizol per 5 mg of tissue and then incubated at room temperature for 5 minutes. 140 μl chloroform was added to the homogenized tissue, which was vortexed and then incubated at room temperature for 2 minutes. The sample was centrifuged for 15 minutes at 12,000×g in a chilled centrifuge (i.e., 5 degrees Celsius). 350 μl of the aqueous phase was collected, to which 525 μl 100% ethanol (or 350 μl 100% isopropanol) was added. The sample was then vortexed and loaded onto a boron carbide column. The column was centrifuged for 30 seconds at 14,000 rpm. The column was washed with 200 μl Column Wash I (CWE; Promega Corporation Z601) and centrifuged for 15 seconds at 14,000 rpm. The column was washed with 500 μl RNA Wash Solution (RWA; Promega Corporation D309) and centrifuged for 30 seconds at 14,000 rpm. The column was washed with 300 μl RWA and centrifuged for 30 seconds at 14,000 rpm. The column was washed with 300 μl RWA and centrifuged for 2 minutes at 14,000 rpm. 50 μl water was used to elute the RNA from the column.

Method for RNA Isolation with Boron Carbide and Lysis in Lysis Buffer and 2% 1-Thioglycerol.

Tissue was suspended in Lysis Buffer (LBA; Promega Corporation Z101) and 2% 1-thioglycerol at 400 μl per 5 mg tissue. The suspended tissue was homogenized for 30 seconds at moderate speed. Debris was cleared by centrifuging for three minutes at 14,000 rpm and the cleared lysate was transferred to a clean tube. 600 μl 100% ethanol (or 400 μl 100% isopropanol) was added to 400 μl lysate, which was then vortexed and loaded onto a boron carbide column. The column was centrifuged for 30 seconds at 14,000 rpm. The column was washed with 200 μl Column Wash I and centrifuged for 15 seconds at 14,000 rpm. The column was washed with 500 μl RWA and centrifuged for 30 seconds at 14,000 rpm. The column was washed with 300 μl RWA and centrifuged for 30 seconds at 14,000 rpm. The column was washed with 300 μl RWA and centrifuged for 2 minutes at 14,000 rpm. 50 μl water was used to elute the RNA from the column.

Preparation of the Boron Carbide Column.

A slurry was prepared by adding powdered boron carbide (i.e., 10 to 14 micron particle size) to a suspension of glass fiber paper (Whatman GF/A) mascaraed in 5 M NaCl at a final concentration of 0.14% (w/v). The glass fiber was added to maintain the flow rate in the final column. The powdered boron carbide was added to a final concentration of 80 mg/mL in the slurry. A plastic column hull (ZSIIC; Promega) was fitted with a 10 micron frit and 350 µl of the prepared slurry was dispensed into the column hull. Vacuum was applied to the column hull at −20 in Hg, thereby drawing the liquid through the column hull and packing the solids into the bottom of the column hull. The packed solids were further compressed by placing a retainer disc composed of woven polyester or polyethylene atop the packed solids and applying 10 lbs. of force. The retainer disc served to prevent movement of the packed solids during the centrifugation steps described in the methods above.

Method for RNA Isolation with A207 and Acid Phenol/Chloroform.

Tissue was homogenized for 30 seconds at moderate speed using 700 µl Trizol per 5 mg tissue. The homogenized tissue was incubated at room temperature for 5 minutes. 140 µl of chloroform was added to the homogenized tissue, which was vortexed and then incubated at room temperature for 2 minutes. The sample was centrifuged for 15 minutes at 12,000×g in a chilled centrifuge (i.e., 5 degrees Celsius). 350 µl of the aqueous phase was collected, to which 350 µl 70% ethanol (or 122 µl 100% isopropanol) was added. The sample was then vortexed and loaded onto an A207 column. The A207 column is packed with a mixture of diatomaceous earth and glass fiber. The column was centrifuged for 30 seconds at 14,000 rpm and the flow through was saved. The flow through was adjusted to 60% ethanol by adding 437.5 µl 100% ethanol (or adjusted to 50% isopropanol by adding 227 µl 100% isopropanol). The adjusted flow through was loaded onto a second A207 column, which was then centrifuged for 30 seconds at 14,000 rpm. The first and second columns were each washed with 200 µl Column Wash I and centrifuged for 15 seconds at 14,000 rpm. Both columns were each washed with 500 µl RWA and centrifuged for 30 seconds at 14,000 rpm. Both columns were each washed with 300 µl RWA and centrifuged for 30 seconds at 14,000 rpm. Both columns were each washed with 300 µl RWA and centrifuged for 2 minutes at 14,000 rpm. RNA was eluted from each column in 50 µl of water.

Method for RNA Isolation with A207 and Lysis in LBA and 2% 1-Thioglycerol.

Tissue was suspended in LBA and 2% 1-thioglycerol at 400 µl per 5 mg tissue. The suspended tissue was homogenized for 30 seconds at moderate speed. Debris was cleared by centrifuging the homogenized tissue for three minutes at 14,000 rpm. The cleared lysate was transferred to a clean tube. 400 µl 70% ethanol (or 140 µl 100% isopropanol) was added to 400 µl lysate, which was then vortexed. 600 µl 100% ethanol (or 400 µl 100% isopropanol) was added to the lysate, which was then vortexed and loaded onto an A207 column. The column was centrifuged for 30 seconds at 14,000 rpm and the flow through was saved. The flow through was adjusted to 60% ethanol by adding 500 µl 100% ethanol (or adjusted to 50% isopropanol by adding 278 µl 100% isopropanol). The adjusted flow through was loaded onto a second A207 column, which was centrifuged for 30 seconds at 14,000 rpm. The first and second columns were DNase treated by adding the following solution: 3 µl DNase, 3 µl 0.09 M MnCl$_2$, and 24 µl yellow core buffer (YCB; Promega Corporation Z317). The columns were incubated for 15 minutes at room temperature with the DNase treatment. Both columns were each washed with 200 µl Column Wash I and centrifuged for 15 seconds at 14,000 rpm. Both columns were washed with 500 µl RWA and centrifuged for 30 seconds at 14,000 rpm. Both columns were washed with 300 µl RWA and centrifuged from 30 seconds at 14,000 rpm. Both columns were washed with 300 µl RWA and centrifuged from 2 minutes at 14,000 rpm. RNA was eluted from each column in 50 µl of water.

Method for RNA Isolation Using miRNeasy and Acid Phenol/Chloroform.

Tissue was homogenized for 30 seconds at moderate speed using 700 µl Trizol per 5 mg tissue. The homogenized tissue was incubated at room temperature for 5 minutes. 140 µl chloroform was added to the homogenized tissue, which was vortexed and then incubated at room temperature for 2 minutes. The sample was centrifuged for 15 minutes at 12,000×g in a chilled centrifuge (i.e., 5 degrees Celsius). 350 µl of the aqueous phase was collected, to which 350 µl of 70% ethanol was added. The sample was vortexed and loaded onto an RNeasy column. The RNeasy column is a silica/glass matrix. The column was centrifuged for 30 seconds at 14,000 rpm and the flow through was saved. The flow through was adjusted to 60% ethanol by adding 450 µl 100% ethanol and loaded an RNeasy MinElute column. The RNeasy MinElute column was designed for small volume elution. The RNeasy MinElute column was centrifuged for 30 seconds at 14,000 rpm. Both columns were washed with 700 µl buffer RWT (Qiagen) and centrifuged for 15 seconds at 14,000 rpm. Both columns were washed with 500 µl RPE (Qiagen) and centrifuged for 15 seconds at 14,000 rpm. The RNeasy column was washed with 500 µl RPE (Qiagen) and centrifuged for 2 minutes for 14,000 rpm. The RNeasy MinElute column was washed with 500 µl 80% ethanol and centrifuged for 2 minutes at 14,000 rpm. RNA was eluted from each column with 50 µl of water.

This two column format allowed for the separation or isolation of large RNAs with the RNeasy column and small RNAs with the RNeasy MinElute column.

Method for RNA Isolation with miRNeasy and Lysis in RLT and 1% β-Mercaptoethanol.

Tissue was suspended in RLT buffer (Qiagen) at 350 µl per 5 mg of tissue. The suspended tissue was homogenized for 30 seconds at moderate speed. Debris was cleared by centrifuging the homogenized tissue for three minutes at 14,000 rpm. The cleared lysate was transferred to a clean tube. 400 µl 70% ethanol (or 140 µl 100% isopropanol) was added to 350 µl lysate, which was then vortexed. 600 µl 100% ethanol (or 400 µl 100% isopropanol) was added to the lysate, followed by vortexing. The sample was loaded onto an RNeasy column. The RNeasy column is a silica/glass matrix. The RNeasy column was centrifuged for 30 seconds at 14,000 rpm and the flow through was saved. The flow through was adjusted to 60% ethanol by the addition of 450 µl 100% ethanol. The adjusted flow through was loaded onto an RNeasy MinElute column, which was centrifuged for 30 seconds at 14,000 rpm. Both columns were washed with 700 µl buffer RWT (Qiagen) and centrifuged for 15 seconds at 14,000 rpm. Both columns were washed with 500 µl RPE (Qiagen) and centrifuged for 15 seconds at 14,000 rpm. The RNeasy column was washed with 500 µl RPE and centrifuged for 2 minutes at 14,000 rpm. The RNeasy MinElute column was washed with 500 µl 80% ethanol and centrifuged for 2 minutes at 14,000 rpm. RNA was eluted from each column with 50 µl of water.

Example 2

Comparison of Boron Carbide, A207, and miRNeasy RNA Isolation Methods

The methods of Example 1 were used to examine whether boron carbide, A207, and miRNeasy could isolate miRNA alone and/or in combination with acid phenol/chloroform extraction. In particular, each method described in Example 1 was employed to isolate RNA from mouse liver and the isolated RNA was examined for the presence of miR21.

FIG. 1 and Table 1 show the detection of miR21 when acid phenol/chloroform extraction was used in combination with each of boron carbide (B4C), A207, and miRNeasy. miR21 was detected in the total RNA fraction when the collected aqueous phase was adjusted to either 60% ethanol or 50% isopropanol in the method using boron carbide (see B4C total 60% EtOH and B4C total 50% IPA, respectively, in FIG. 1 and Table 1).

For both the A207 and miRNeasy sample sets, three fractions were available for analysis: total RNA, large RNA, and small RNA. The fraction containing total RNA was obtained with a single addition of ethanol to a final concentration of 60%, followed by loading onto a single column (see A207 total 60% EtOH and miRNeasy Total in FIG. 1 and Table 1). The fraction containing large RNA was obtained by addition of ethanol to a final concentration of 35%, followed by passage over an RNeasy column, in which the collected flowthrough contained the large RNA (see A207 large 35% EtOH and miRNeasy Large in FIG. 1 and Table 1). The fraction containing the small RNA was obtained by adjusting the flowthrough containing the large RNA with addition of ethanol to a final concentration of 60%, followed by loading onto a second A207 or MinElute column (see A207 miRNA 60% EtOH and miRNeasy in FIG. 1 and Table 1).

Regarding the method utilizing A207, miR21 was detected in isolated total RNA and small RNA, but less miR21 was detected in isolated large RNA. A similar result was obtained with miRNeasy, in which miR21 was detected in isolated total RNA and small RNA, but less miR21 was detected in isolated large RNA.

A comparison of the above results, in which acid phenol/chloroform extraction was utilized in the isolation method, demonstrated that boron carbide achieved about 85% purification as compared to competing methods (e.g., miRNeasy).

TABLE 1

Copies of miR21 in each isolated RNA sample obtained with acid/phenol chloroform extraction

| Isolated RNA | Copies × $10^3$ of miR21 |
|---|---|
| B4C total 60% EtOH | 122.3 |
| B4C total 50% IPA | 133.2 |
| A207 total 60% EtOH | 121.6 |
| A207 large 35% EtOH | 1.0 |
| A207 miRNA 60% EtOH | 158.7 |
| miRNeasy Total | 158.9 |
| miRNeasy Large | 10.9 |
| miRNeasy miRNA | 140.7 |

Figure 2:
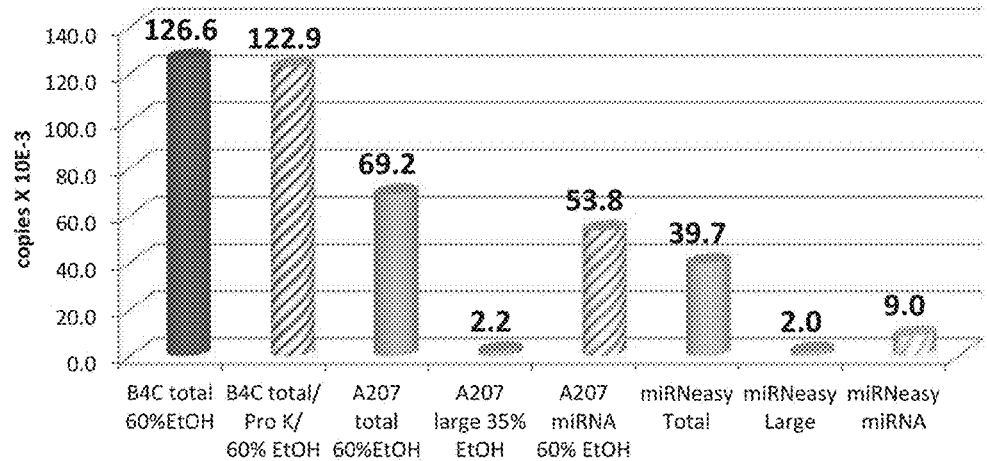
FIG. 2 shows detection of miR21 from RNA isolated with each of boron carbide, A207, and miRNeasy.

FIG. 2 and Table 2 show the detection of miR21 when acid phenol/chloroform extraction was not used in combination with each of boron carbide, A207, and miRNeasy. The sample nomenclature used in FIG. 2 and Table 2 is the same as that used in FIG. 1 and Table 1. miR21 was detectable when the collected aqueous phase was adjusted to either 60% ethanol or 50% isopropanol in the method using boron carbide. In the method utilizing A207, miR21 was detected in the isolated total RNA and small RNA, but less miR21 was detected in the isolated large RNA. In the miRNeasy method, miR21 was detected in the isolated total RNA, but detected in smaller quantities in the isolated large and small RNA. These data demonstrated that the method using boron carbide, unlike the methods employing A207 and miRNeasy, is able to yield similar or consistent quantities of small RNA (e.g., miR21) regardless if acid phenol/chloroform extraction is performed prior to loading the sample on the column. Boron carbide, unlike A207 and miRNeasy, yields significantly larger quantities of small RNA in the absence of an acid phenol/chloroform extraction step.

TABLE 2

Copies of miR21 in each isolated RNA sample obtained without acid phenol/cholorform extraction

| Isolated RNA | Copies × $10^3$ of miR21 |
|---|---|
| B4C total 60% EtOH | 126.6 |
| B4C total 50% IPA | 122.9 |
| A207 total 60% EtOH | 69.2 |
| A207 large 35% EtOH | 2.2 |
| A207 miRNA 60% EtOH | 53.8 |
| miRNeasy Total | 39.7 |
| miRNeasy Large | 2.0 |
| miRNeasy miRNA | 9.0 |

Example 3

Materials and Methods for Example 4

Boron Carbide. Boron carbide was obtained from UK Abrasives, Inc. The grades of boron carbide used were each assigned an "F" value based upon the Federation of European Producers of Abrasives (FEPA). These "F" values are also known as microgrits given the small size of these grades of boron carbide. The mean boron carbide particle sizes tested are listed in Table 3.

TABLE 3

Mean Boron Carbide Particle Size Relative to "F" Value

| Mean Particle Size in Microns | "F" Value |
|---|---|
| 47 | F240 |
| 39 | F280 |
| 13 | F500 |
| 4.4 | F1000 |
| 3.3 | F1200 |
| 2.3 | F1500 |

Preparation of the Columns with Packed Beds of Boron Carbide Particles.

Stocks of the boron carbide microgrits were prepared by suspension of the boron carbide particles in water at a final concentration of 120 mg/mL. Stocks were generated for each of the microgrits listed in Table 3. 200 µL aliquots of these stocks were dispensed into respective empty plastic columns. Each column had first been fitted with a 10 µm polyethylene frit. After dispensing of the aliquots into the columns, vacuum was applied at −20 Hg until the liquid was gone. Each resin bed was further compacted with a force gauge set to 6 lbf.

Homogenate Preparation.

A mouse liver homogenate was prepared by suspending the tissue in LBA+2% 1-thioglycerol at a final concentration of 25 mg/mL. A tissue tearor mechanical homogenizer was used to homogenize the tissue for 30 seconds. 200 µL of this homogenate was dispensed into 1.5 mL tubes for use in the first binding reaction described below in Example 4.

Example 4

Two-Step Enrichment for miRNAs Using Columns Having Packed Beds of Boron Carbide Particles As described above, boron carbide was used to isolate RNA, including miRNA, from tissue. To further examine the capabilities of boron carbide in RNA isolation, different microgrits were tested in a two-step method. The two step method first bound the RNA to boron carbide in the presence of a final concentration of 25% v/v isopropanol and then bound the RNA in the presence of a final concentration of 50% v/v isopropanol.

First Binding Reaction in the Presence of 25% v/v Isopropanol.

For the first binding reaction, 100% isopropanol was added to the dispensed homogenate such that the final concentration of isopropanol was 25% v/v in each resulting reaction volume. The reaction volumes were vortexed and transferred to columns having packed boron carbide particles. The columns were centrifuged at 14,000 revolutions per minute (rpm) for one minute. Flowthroughs from the columns were collected for use in a second binding reaction, which is described below in more detail.

The columns were then each washed once with 500 µL of RWA (60 mM potassium acetate (KOAc), 10 mM tris (hydroxymethyl)aminomethane (Tris), 60% ethanol, pH 7.5). The columns were cleared of the wash by centrifuging the columns at 14,000 rpm for one minute. 50 µL of a solution containing 5 µL RQ1 DNAse, 5 µL 90 mM Manganese Chloride ($MnCl_2$), and 40 µL of yellow core buffer (1.125 M Sodium Chloride (NaCl), 22.5 mM Tris, pH 7.5, and 0.0025% FD&C Yellow #5) was applied to the top of each packed column. The columns were incubated for 15 minutes at room temperature with this solution. Then, 200 µL of a solution containing 2.8 M guanidine-HCl and 60% ethanol was applied to each packed column. The columns were centrifuged at 14,000 rpm for one minute. Two additional washes, each with 500 µL RWA, were done for each column. The columns were centrifuged at 14,000 rpm for one minute to clear each wash. The columns were then dried by further centrifugation for two minutes at 14,000 rpm. RNA was eluted from each column with 50 µL of water to yield the isolated RNA.

Figure 3:
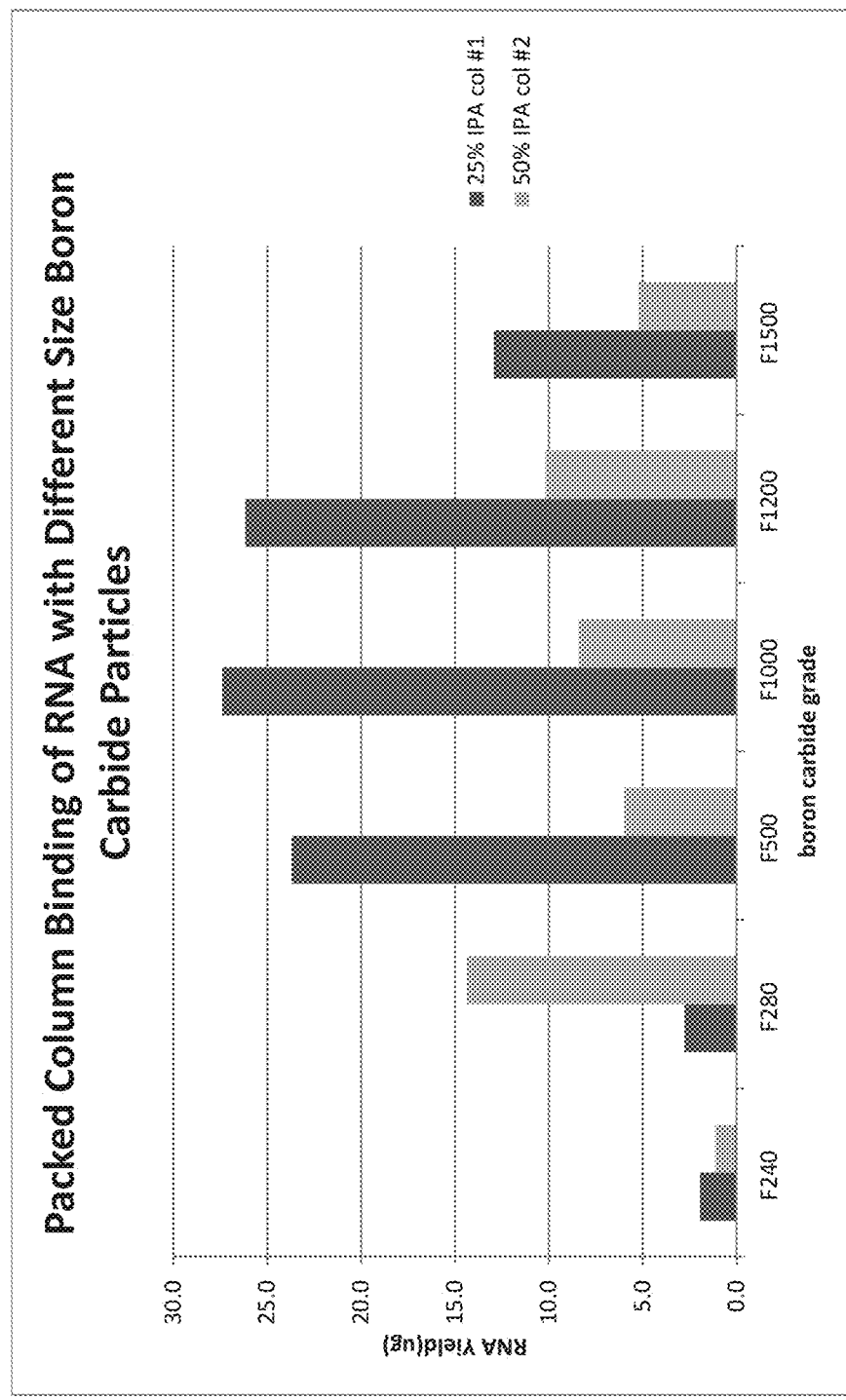
FIG. 3 shows binding of RNA to different sizes of boron carbide particles packed in a column.

For each microgrit tested, the RNA yield in micrograms (µg) from this first binding reaction is shown in FIG. 3. As shown in FIG. 3, more than 25 µg of RNA was isolated when the microgrits F1000 and F1200 were used in combination with 25% v/v isopropanol. More than 20 µg of RNA was isolated when the microgrit F500 was used in combination with 25% v/v isopropanol. More than 10 µg of RNA was isolated when the microgrit F1500 was used in combination with 25% v/v isopropanol. Less than 5 µg of RNA was isolated when the microgrits F240 and F280 were used in combination with 25% v/v isopropanol. Accordingly, the microgrits, in order of largest RNA yield to smallest RNA yield for the first binding reaction, were as follows: F1000, F1200, F500, F1500, F280, and F240.

Second Binding Reaction in the Presence of 50% v/v Isopropanol.

Stocks of the boron carbide microgrits were prepared by suspension of the boron carbide particles in water at a final concentration of 120 mg/mL. Stocks were generated for each of the microgrits listed in Table 3. 200 µL aliquots of these suspensions were dispensed into respective 1.5 mL Eppendorf tubes. The Eppendorf tubes were centrifuged at 14,000 rpm for 2 minutes. 150 µL of each supernatant was removed, thereby concentrating the respective 24 mg of microgrit in a 50 µL volume. Flowthroughs from the first binding reactions described above were each transferred to the same type of boron carbide microgrit used in the first binding reaction (e.g., flowthrough from a first binding reaction with F240 microgrit was transferred to F240 microgrit for a second binding reaction).

100% isopropanol was then added such that the final concentration of isopropanol was 50% v/v in each resulting reaction volume. The reaction volumes were vortexed and then placed in an Eppendorf Thermomixer for 15 minutes at 20° C. and 14,000 rpm. The microgrits were then collected by transferring each reaction volume to an empty plastic column fitted with a 10 µm polyethylene frit. The columns were centrifuged at 14,000 rpm for one minute. The flowthroughs were discarded.

The columns were then each washed once with 500 µL of RWA (60 mM potassium acetate (KOAc), 10 mM tris (hydroxymethyl)aminomethane (Tris), 60% ethanol, pH 7.5). The columns were cleared of the wash by centrifuging the columns at 14,000 rpm for one minute. 50 µL of a solution containing 5 µL RQ1 DNAse, 5 µL 90 mM Manganese Chloride ($MnCl_2$), and 40 µL of yellow core buffer (1.125 M Sodium Chloride (NaCl), 22.5 mM Tris, pH 7.5, and 0.0025% FD&C Yellow #5) was applied to each column. The columns were incubated for 15 minutes at room temperature with this solution. Then, 200 µL of a solution containing 2.8 M guanidine-HCl and 60% ethanol was applied to each packed column. The columns were centrifuged at 14,000 rpm for one minute. Two additional washes, each with 500 µL RWA, were done for each column. The columns were centrifuged at 14,000 rpm for one minute to clear each wash. The columns were then dried by further centrifugation for two minutes at 14,000 rpm. RNA was eluted from each column with 50 µL of water to yield the isolated RNA.

For each microgrit tested, the RNA yield in micrograms (n) from this second binding reaction is shown in FIG. 3. As shown in FIG. 3, more than 10 µg of RNA was isolated when the microgrit F280 was used in combination with 50% v/v isopropanol in the second binding reaction. More than 5 µg of RNA was isolated when the microgrits F500, F1000, and F1200 were used in combination with 50% v/v isopropanol in the second binding reaction. About 5 µg of RNA was isolated when the microgrit F1500 was used in combination with 50% v/v isopropanol in the second binding reaction. Less than 5 µg of RNA was isolated when the microgrit F240 was used in combination with 50% v/v isopropanol in the second binding reaction. Accordingly, for the second binding reaction, the microgrits, in order of largest RNA yield to smallest RNA yield for the second binding reaction, were as follows: F280, F1200, F1000, F500, F1500, and F240.

In summary, the above two-step method demonstrated that RNA could be isolated with differently sized boron carbide particles, though the amount of RNA isolated varied depending on the size of the boron carbide particle as shown in FIG. 3. Additionally, RNA could be isolated when the boron carbide particles were packed into a column. Additional RNA could be isolated by performing a second binding reaction with the flowthrough from the first binding reaction.

Example 5

Detection of miR21 in RNA Isolated with the Two-Step Method of Example 4

To determine how miRNAs partitioned in the two-step method of Example 4, reverse transcriptase-quantitative polymerase chain reaction (RT-qPCR) assays were employed to detect miR21 in the eluates shown in FIG. 3.

10 ng of template was used for each reverse transcriptase (RT) reaction. The RT and polymerase chain reaction (PCR) primer sets targeting miR21 were purchased from Life Technologies as were the TaqMan™ miRNA RT kits. Reaction conditions were those suggested by the manufacturer for 15 μL RT reactions. Standards were prepared using acid-phenol extracted total RNA from mouse liver.

1.33 μL of each RT reaction was used for a respective 20 μL qPCR reaction. The qPCR reactions were performed using the reaction setup and cycling conditions suggested by Life Technologies for use of the kit. A Stratagene 3005P thermocycler was used for amplification and Cq values were calculated using built-in software associated with the Stratagene 3005P thermocycler based upon the standards used in the assay.

Figure 4:
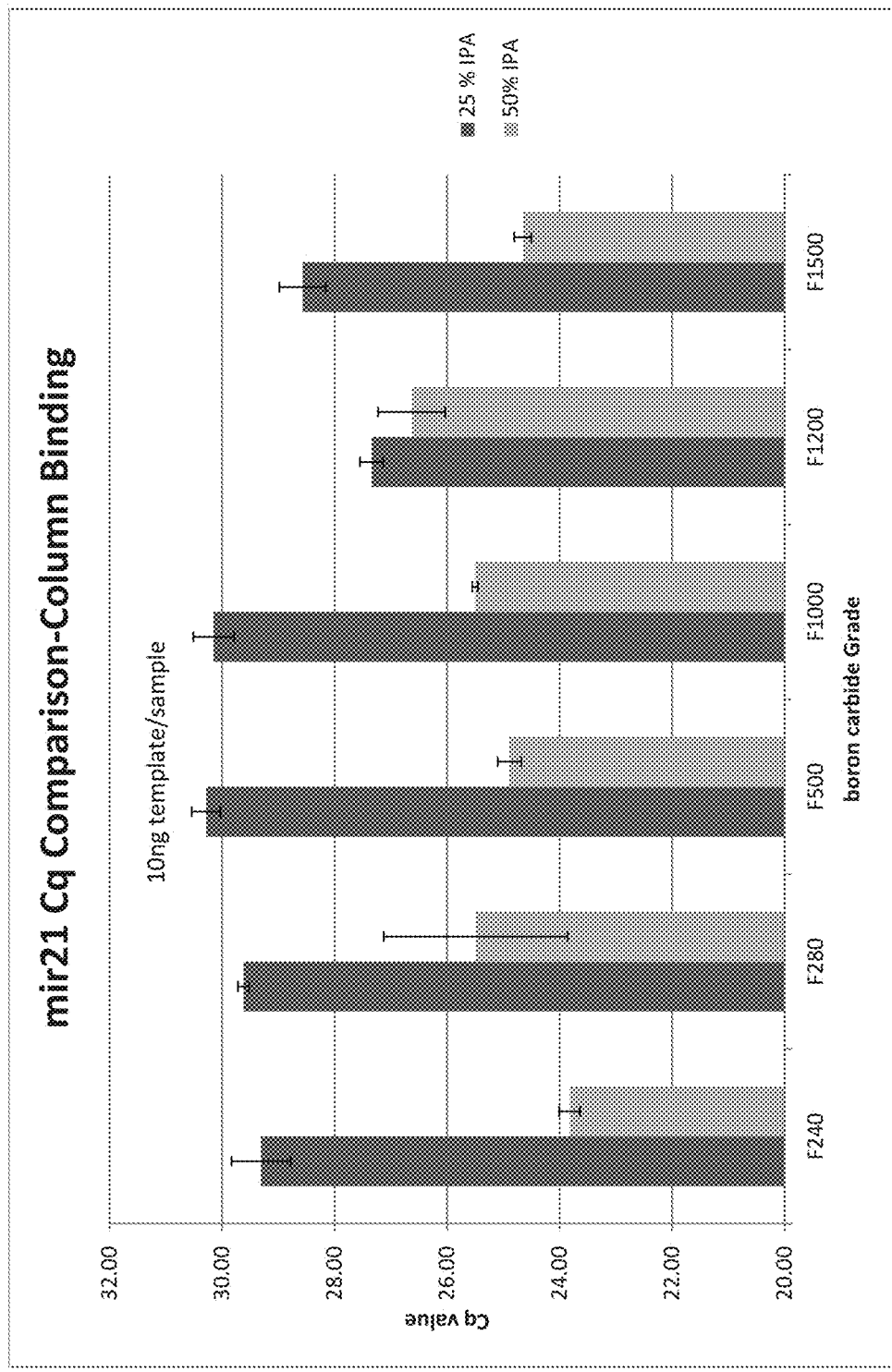
FIG. 4 shows detection of miR21 from RNA that was isolated with different sizes of boron carbide particles packed in a column and in the presence of 25% isopropanol (25% IPA) or 50% isopropanol (50% IPA).

The results of the RT-qPCR assays are shown in FIG. 4. miR21 was present in each eluate (resulting from the first binding reaction) though the amount of miR21 varied with the particle size of the boron carbide used in the isolation. miR21 was also present in each eluate (resulting from the second binding reaction) though again the amount of miR21 varied with the particle size of the boron carbide used in the isolation. These data showed that miR21 could be isolated using boron carbide particles packed in a column and in combination with 25% v/v isopropanol and 50% v/v isopropanol. Additional miR21 was isolated by performing the second binding reaction. Accordingly, the two-step method of Example 4 resulted in the isolated of miRNAs (e.g., miR21), in which the second binding reaction permitted capture of miRNAs that had not been captured by the first binding reaction, thereby increasing the amount of miRNA isolated from the homogenate.

Example 6

Materials and Method for Example 7

Boron Carbide.

Boron carbide was obtained from UK Abrasives, Inc. The grades of boron carbide used were each assigned an "F" value based upon the Federation of European Producers of Abrasives (FEPA). These "F" values are also known as microgrits given the small size of these grades of boron carbide. The mean boron carbide particle sizes tested are listed above in Table 3.

Boron Carbide Stocks.

Stocks of the boron carbide microgrits listed in Table 3 were prepared by suspending each microgrit in water at a final concentration of 120 mg/mL. 200 μL aliquots of these suspensions were dispensed into respective 1.5 mL Eppendorf tubes. The Eppendorf tubes were then centrifuged at 14,000 rpm for two minutes. 150 μL of the supernatant was removed from each Eppendorf tube, thereby concentrating each 24 mg of microgrit in a volume of 50 μL.

Homogenate Preparation.

A mouse liver homogenate was prepared by suspending the tissue in LBA+2% 1-thioglycerol at a final concentration of 25 mg/mL. A tissue tearor mechanical homogenizer was used to homogenize the tissue for 30 seconds.

Example 7

Two-Step Enrichment for miRNAs Using Suspensions of Boron Carbide Particles

As described above, a two-step method using boron carbide particles packed within columns resulted in the isolation of RNA, including miRNAs. The two-step method of RNA isolation was further examined by using suspensions of boron carbide particles in lieu of the columns having the packed beds of boron carbide particles. Again, the two step method first bound the RNA to boron carbide in the presence of a final concentration of 25% v/v isopropanol and then bound the RNA in the presence of a final concentration of 50% v/v isopropanol.

First Binding Reaction in the Presence of 25% v/v Isopropanol.

200 μL of the homogenate was added to the concentrated microgrits (see description above in Example 6) and the resulting mixture was vortexed. 100% isopropanol was added such that the final concentration of isopropanol was 25% v/v in the resulting reaction volume. The reaction volumes were vortexed and placed in an Eppendorf Thermomixer for 15 minutes at 20° C. and 14,000 rpm. The boron carbide particles were collected by transferring the reaction volumes to empty plastic columns, each fitted with a 10 μm polyethylene frit. The columns were centrifuged at 14,000 rpm for one minute. Flowthroughs were collected for the second binding reactions, which are described below in more detail.

The columns were then each washed once with 500 μL of RWA (60 mM potassium acetate (KOAc), 10 mM tris (hydroxymethyl)aminomethane (Tris), 60% ethanol, pH 7.5). The columns were cleared of the wash by centrifuging the columns at 14,000 rpm for one minute. 50 μL of a solution containing 5 μL RQ1 DNAse, 5 μL 90 mM Manganese Chloride ($MnCl_2$), and 40 μL of yellow core buffer (1.125 M Sodium Chloride (NaCl), 22.5 mM Tris, pH 7.5, and 0.0025% FD&C Yellow #5) was applied to each column. The columns were incubated for 15 minutes at room temperature with this solution. Then, 200 μL of a solution containing 2.8 M guanidine-HCl and 60% ethanol was applied to each column. The columns were centrifuged at 14,000 rpm for one minute. Two additional washes, each with 300 μL RWA, were done for each column. The columns were centrifuged at 14,000 rpm for one minute to clear each wash. The columns were then dried by further centrifugation for two minutes at 14,000 rpm. RNA was eluted from each column with 50 μL of water to yield the isolated RNA.

Figure 5:
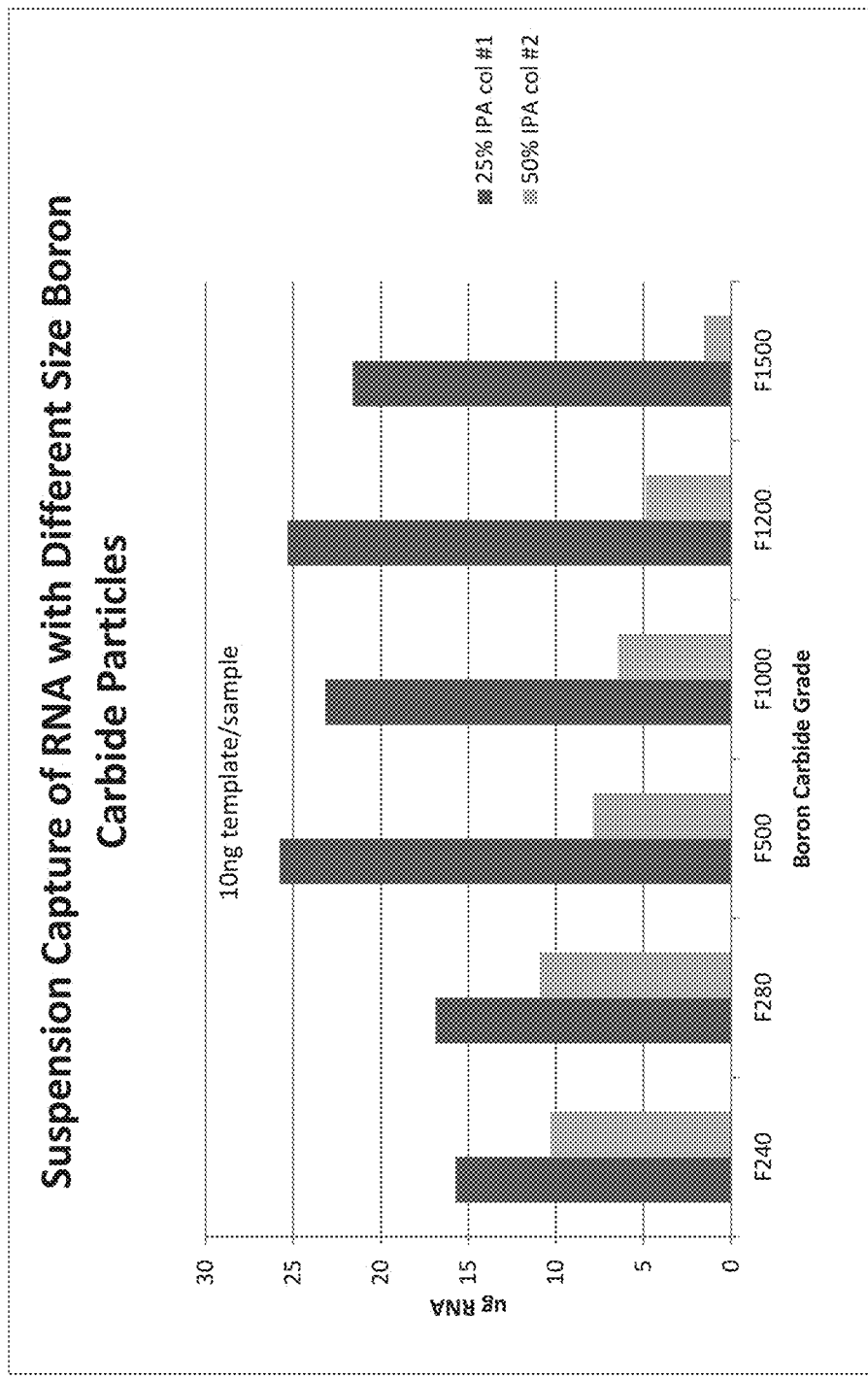
FIG. 5 shows binding of RNA to different sizes of boron carbide particles that are in suspension.

For each microgrit tested, the RNA yield in micrograms (μg) from this first binding reaction is shown in FIG. 5. As shown in FIG. 5, more than 25 μg of RNA was isolated when the microgrit F500 was used in combination with 25% v/v isopropanol. About 25 μg of RNA was isolated when the microgrit F1200 was used in combination with 25% v/v isopropanol. More than 20 μg of RNA was isolated when the microgrits F1000 and F1500 were used in combination with 25% v/v isopropanol. More than 15 μg of RNA was isolated when the microgrits F240 and F280 were used in combination with 25% v/v isopropanol. Accordingly, the microgrits, in order of largest RNA yield to smallest RNA yield for the first binding reaction, were as follows: F500, F1200, F1000, F1500, F280, and F240.

Second Binding Reaction in the Presence of 50% v/v Isopropanol.

Flowthroughs from the first binding reactions were each transferred to the concentrated microgrits (see description above in Example 6). In particular, each flowthrough was transferred to the same type of boron carbide microgrit used in the first binding reaction (e.g., flowthrough from a first binding reaction with F240 microgrit was transferred to F240 microgrit for a second binding reaction).

100% isopropanol was then added such that the final concentration of isopropanol was 50% v/v in each resulting reaction volume. The reaction volumes were vortexed and then placed in an Eppendorf Thermomixer for 15 minutes at 20° C. and 14,000 rpm. The microgrits were then collected by transferring each reaction volume to an empty plastic column fitted with a 10 μm polyethylene frit. The columns were centrifuged at 14,000 rpm for one minute. The flowthroughs were discarded.

The columns were then each washed once with 500 μL of RWA (60 mM potassium acetate (KOAc), 10 mM tris (hydroxymethyl)aminomethane (Tris), 60% ethanol, pH 7.5). The columns were cleared of the wash by centrifuging the columns at 14,000 rpm for one minute. 50 μL of a solution containing 5 μL RQ1 DNAse, 5 μL 90 mM Manganese Chloride ($MnCl_2$), and 40 μL of yellow core buffer (1.125 M Sodium Chloride (NaCl), 22.5 mM Tris, pH 7.5, and 0.0025% FD&C Yellow #5) was applied to each column. The columns were incubated for 15 minutes at room temperature with this solution. Then, 200 μL of a solution containing 2.8 M guanidine-HCl and 60% ethanol was applied to each column. The columns were centrifuged at 14,000 rpm for one minute. Two additional washes, each with 300 μL RWA, were done for each column. The columns were centrifuged at 14,000 rpm for one minute to clear each wash. The columns were then dried by further centrifugation for two minutes at 14,000 rpm. RNA was eluted from each column with 50 μL of water to yield the isolated RNA.

For each microgrit tested, the RNA yield in micrograms (n) from the second binding reaction is shown in FIG. 5. As shown in FIG. 5, more than 10 μg of RNA was isolated when the microgrit F280 was used in combination with 50% v/v isopropanol. About 10 μg of RNA was isolated when the microgrit F240 was used in combination with 50% isopropanol. More than 5 μg of RNA was isolated when the microgrits F500 and F1000 were used in combination with 50% isopropanol. Less than 5 μg of RNA was isolated when the microgrits F1200 and F1500 were used in combination with 50% v/v isopropanol. Accordingly, the microgrits, in order of largest RNA yield to smallest RNA yield for the second binding reaction, were as follows: F280, F240, F500, F1000, F1200, and F1500.

In summary, the above two-step method demonstrated that RNA could be isolated with differently sized boron carbide particles, though the amount of RNA isolated varied depending on the size of the boron carbide particle as shown in FIG. 5. Additionally, RNA could be isolated when the boron carbide particles were in suspension for both steps of the method. Additional RNA could be isolated by performing a second binding reaction with the flowthrough from the first binding reaction.

Example 8

Detection of miR21 in RNA Isolated with the Two-Step Method of Example 7

To determine how miRNAs partitioned in the two-step method of Example 7, reverse transcriptase-quantitative polymerase chain reaction (RT-qPCR) assays were employed to detect miR21 in the eluates shown in FIG. 5.

10 ng of template was used for each reverse transcriptase (RT) reaction. The RT and polymerase chain reaction (PCR) primer sets targeting miR21 were purchased from Life Technologies as were the TaqMan™ miRNA RT kits. Reaction conditions were those suggested by the manufacturer for 15 μL RT reactions. Standards were prepared using acid-phenol extracted total RNA from mouse liver.

1.33 μL of each RT reaction was used for a respective 20 μL qPCR reaction. The qPCR reactions were performed using the reaction setup and cycling conditions suggested by Life Technologies for use of the kit. A Stratagene 3005P thermocycler was used for amplification and Cq values were calculated using built-in software associated with the Stratagene 3005P thermocycler based upon the standards used in the assay.

Figure 6:
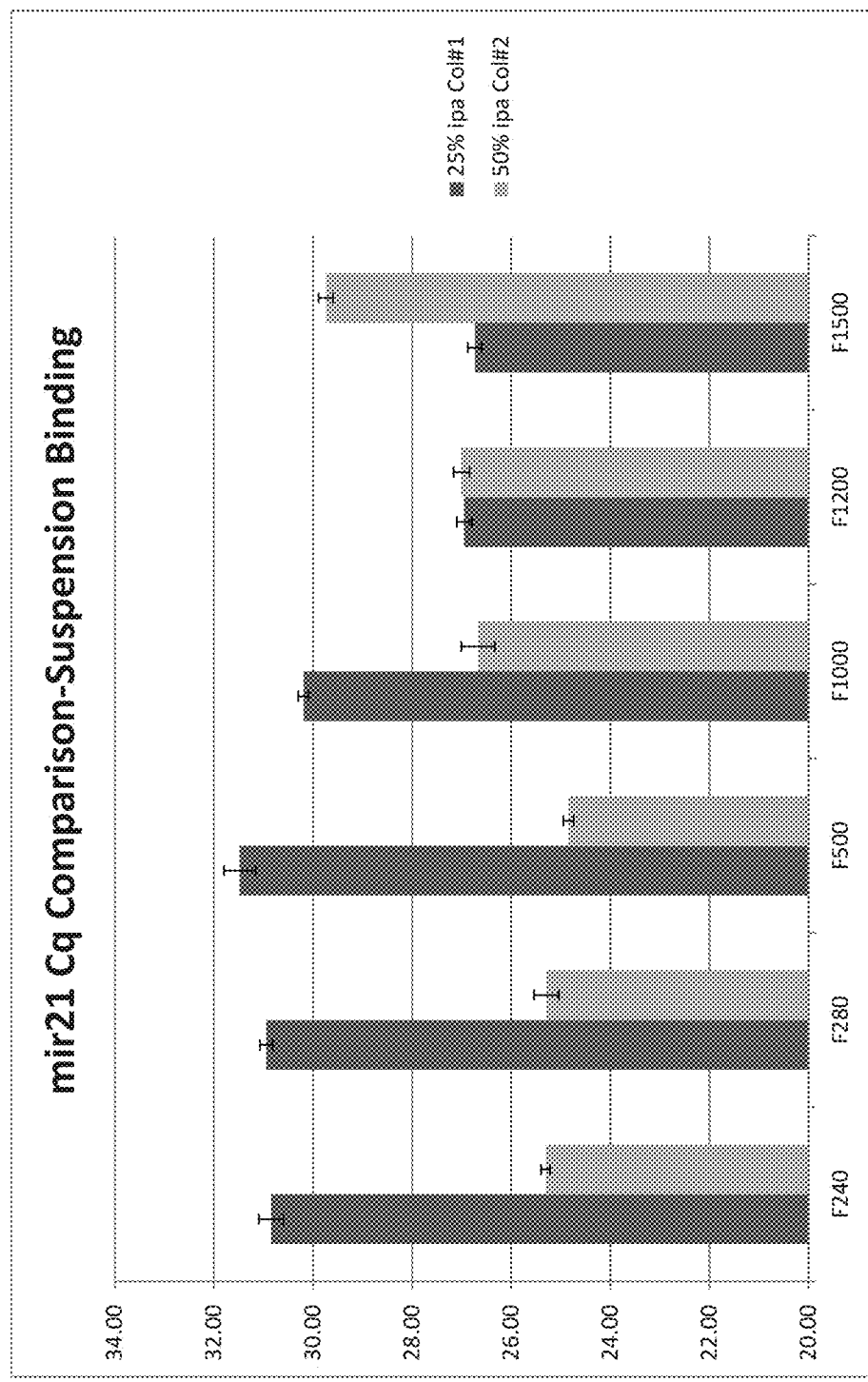
FIG. 6 shows detection of miR21 from RNA that was isolated with different sizes of boron carbide particles in suspension and in the presence of 25% isopropanol (25% IPA) or 50% isopropanol (50% IPA).

The results of the RT-qPCR assays are shown in FIG. 6. miR21 was present in each eluate (resulting from the first binding reaction) though the amount of miR21 varied with the particle size of the boron carbide used in the isolation. miR21 was also present in each eluate (resulting from the second binding reaction) though again the amount of miR21 varied with the particle size of the boron carbide used in the isolation. These data showed that miR21 could be isolated using boron carbide particles in suspension and in combination with 25% v/v isopropanol and 50% v/v isopropanol. Additional miR21 was isolated by performing the second binding reaction. Accordingly, the two-step method of Example 7 resulted in the isolation of miRNAs (e.g., miR21), in which the second binding reaction permitted capture of miRNAs that had not been captured by the first binding reaction, thereby increasing the amount of miRNA isolated from the homogenate.

Example 9

Materials and Methods for Example 10

Boron Carbide Stock Boron carbide was obtained from UK Abrasives, Inc. Specifically, the boron carbide microgrit F500 (i.e., 13 μm particle size) was used for the comparison described below in Example 10 because F500 provided consistent flow rates and column retention. Stock of the F500 microgrit was prepared by suspending the boron carbide particles in water at a final concentration of 120 mg/mL. 200 μL aliquots of this suspension were dispensed into 1.5 mL Eppendorf tubes. The Eppendorf tubes were centrifuged at 14,000 rpm for two minutes. 150 μL of supernatant was removed, thereby concentrating each 24 mg of boron carbide particles in a volume of 50 μL.

Homogenate Preparation.

A mouse liver homogenate was prepared by suspending the tissue in LBA+2% 1-thioglycerol at a final concentration of 25 mg/mL. A tissue tearor mechanical homogenizer was used to homogenize the tissue for 30 seconds.

Example 10

Ethanol Vs. Isopropanol in Binding of RNA to Suspended Boron Carbide Particles

As described above, RNA was bound to the boron carbide particles in the presence of isopropanol. To determine if RNA could bind boron carbide in the presence of other alcohols, e.g., ethanol, the binding of RNA to boron carbide was compared in the presence of different concentrations of isopropanol and ethanol.

Specifically, 200 μL of the homogenate was added to the concentrated microgrits (see description above in Example 9) and the resulting mixtures were vortexed. For the binding reactions, 100% isopropanol or 100% ethanol was added such that the final concentration was 10% v/v, 12.5% v/v, 15% v/v, 17.5% v/v, 20% v/v, 25% v/v, 30% v/v, 35% v/v, 40% v/v, 45% v/v, 50% v/v, 55% v/v, 60% v/v, or 65% v/v in the resulting reaction volumes. The reaction volumes were vortexed and placed in an Eppendorf Thermomixer for 15 minutes at 20° C. and 14,000 rpm. Boron carbide particles were collected by transferring the reaction volumes to empty plastic columns, each fitted with a 10 μm polyethylene frit. The columns were then centrifuged at 14,000 rpm for one minute.

The columns were then each washed once with 500 μL of RWA (60 mM potassium acetate (KOAc), 10 mM tris (hydroxymethyl)aminomethane (Tris), 60% ethanol, pH 7.5). The columns were cleared of the wash by centrifuging the columns at 14,000 rpm for one minute. 50 μL of a solution containing 5 μL RQ1 DNAse, 5 μL 90 mM Manganese Chloride ($MnCl_2$), and 40 μL of yellow core buffer (1.125 M Sodium Chloride (NaCl), 22.5 mM Tris, pH 7.5, and 0.0025% FD&C Yellow #5) was applied to each column. The columns were incubated for 15 minutes at room temperature with this solution. Then, 200 μL of a solution containing 2.8 M guanidine-HCl and 60% ethanol was applied to each column. The columns were centrifuged at 14,000 rpm for one minute. Two additional washes, each with 300 μL RWA, were done for each column. The columns were centrifuged at 14,000 rpm for one minute to clear each wash. The columns were then dried by further centrifugation for two minutes at 14,000 rpm. RNA was eluted from each column with 50 μL of water to yield the isolated RNA.

Figure 7:
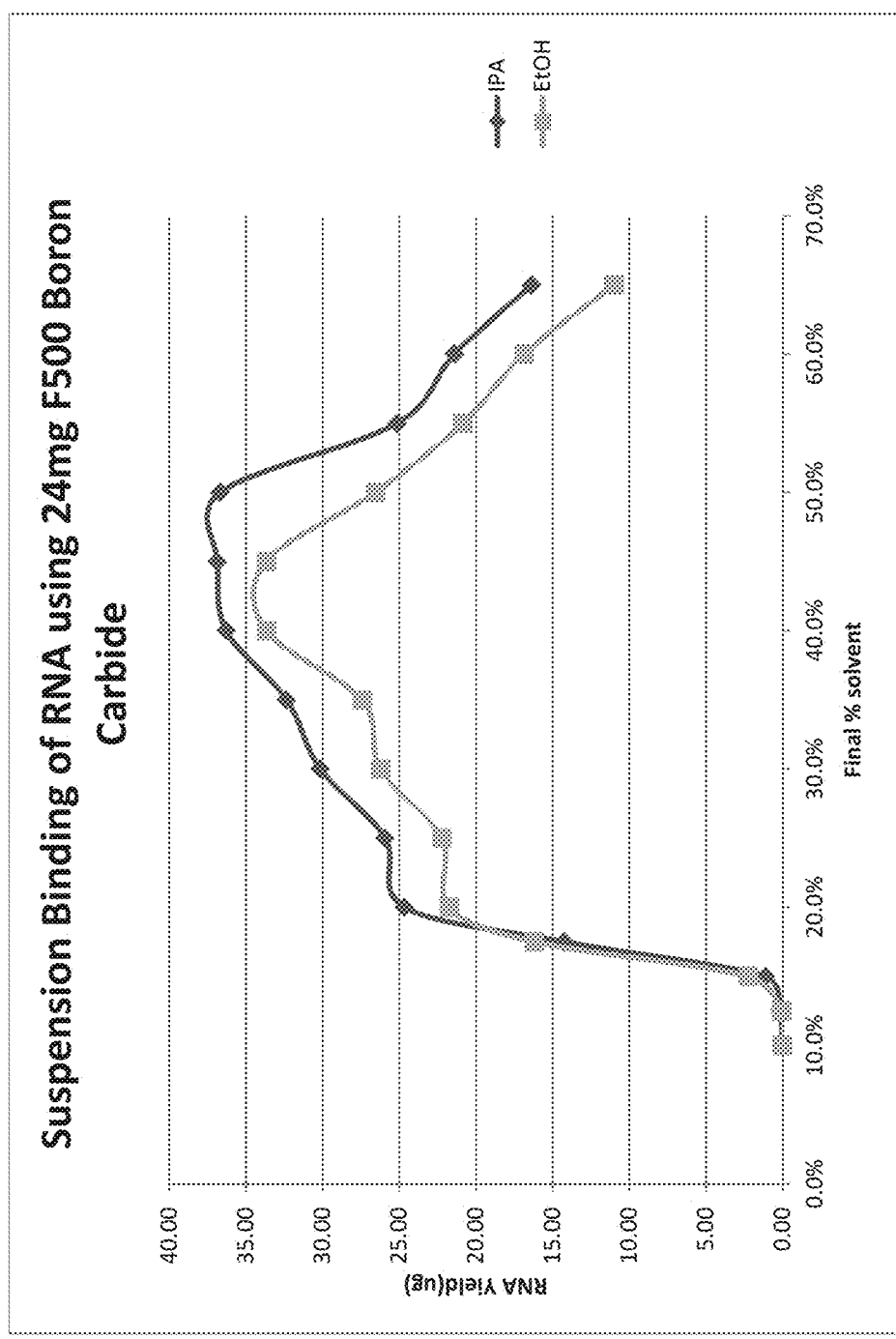
FIG. 7 shows binding of RNA to F500 boron carbide particles in suspension and in the presence of isopropanol (IPA; diamonds) or ethanol (EtOH; squares).

For each final concentration of isopropanol or ethanol tested, the RNA yield in micrograms (μg) is shown in FIG. 7. At lower concentrations (i.e., less than 20% v/v), use of ethanol or isopropanol resulted in similar yields of RNA. Between about 20% v/v and 65% v/v, use of isopropanol gave higher yields of RNA as compared to ethanol though both alcohols facilitated the isolation of significant quantities of RNA. Accordingly, these data showed that boron carbide can be utilized to isolate RNA with either isopropanol or ethanol being present during binding of the RNA to the boron carbide. Additionally, final concentrations of about 17.5% v/v to about 65% v/v of either isopropanol or ethanol during binding of the RNA to the boron carbide allowed for isolation of 10 μg RNA or greater.

For reasons of completeness, various aspects of the present disclosure are set out in the following numbered clauses:

Clause 1. A method for isolating nucleic acids from a sample, the method comprising:
(a) contacting the sample with a boron carbide composition under conditions sufficient to form a boron carbide-nucleic acid complex;
(b) separating the complex from the sample; and
(c) eluting the nucleic acids from the complex, thereby isolating the nucleic acids.

Clause 2. The method of clause 1, wherein the sample is prepared in the absence of an organic extraction.

Clause 3. The method of clause 2, wherein the organic extraction comprises phenol and chloroform.

Clause 4. The method of clause 3, wherein the phenol is an acid phenol.

Clause 5. The method of any one of clauses 1-4, further comprising contacting the sample with a chaotrope.

Clause 6. The method of clause 5, wherein the chaotrope is present in a lysis or binding buffer.

Clause 7. The method of clause 5 or clause 6, wherein the chaotrope is guanidine thiocyanate (GTC) or guanidine hydrochloride (GHCl).

Clause 8. The method of any one of clauses 1-7, wherein the boron carbide composition further comprises glass fibers.

Clause 9. The method of any one of clauses 1-8, wherein the boron carbide-nucleic acid complex is formed in the presence of an alcohol.

Clause 10. The method of clause 9, wherein the alcohol is isopropanol or ethanol.

Clause 11. The method of any one of clauses 1-10, wherein formation of the boron carbide-nucleic acid complex comprises selective binding of the nucleic acid to the boron carbide and wherein selective binding is dependent upon a concentration of an alcohol.

Clause 12. The method of clause 11, wherein the alcohol is isopropanol or ethanol.

Clause 13. The method of any one of clauses 9-12, wherein the nucleic acid is RNA and wherein the RNA selectively binds the boron carbide when the concentration of alcohol is from about 15% v/v to about 100% v/v.

Clause 14. The method of clause 13, wherein the RNA is large RNA and wherein the large RNA selectively binds the boron carbide when the concentration of isopropanol is from about 15% to about 20%.

Clause 15. The method of clause 13, wherein the RNA is large RNA and wherein the large RNA selectively binds the boron carbide when the concentration of ethanol is from about 20% v/v to about 35% v/v.

Clause 16. The method of clause 13, wherein the RNA is small RNA and wherein the small RNA selectively binds the boron carbide when the concentration of isopropanol is about 40% v/v to about 60% v/v.

Clause 17. The method of clause 13, wherein the RNA is small RNA and wherein the small RNA selectively binds the boron carbide when the concentration of ethanol is about 50% v/v to about 70% v/v.

Clause 18. The method of clause 14, wherein the RNA is long, noncoding RNA.

Clause 19. The method of clause 16 or clause 17, wherein the small RNA is selected from the group consisting of microRNA (miRNA), small interfering RNA (siRNA), piwi-interacting RNA (piRNA), small noncoding RNA, small nuclear RNA (snRNA), small nucleolar RNA (snoRNA), and transfer RNA (tRNA).

Clause 20. The method of any one of clauses 16, 17, or 19, wherein the small RNA is miRNA.

Clause 21. The method of any one of clauses 1-20, wherein the nucleic acid is RNA.

Clause 22. The method of clause 21, wherein the RNA is small RNA.

Clause 23. The method of clause 21, wherein the RNA is microRNA (miRNA).

Clause 24. The method of clause 21, wherein the RNA comprises RNA molecules having a length of about 5 nucleotides to about 200 nucleotides.

Clause 25. The method of clause 24, wherein the RNA comprises RNA molecules having a length of about 10 nucleotides to about 100 nucleotides.

Clause 26. The method of clause 24, wherein the RNA comprises RNA molecules having a length of about 18 nucleotides to about 30 nucleotides.

Clause 27. The method of any one of clauses 1-26, wherein the boron carbide has a particle size of about 1 micron to about 20 microns.

Clause 28. The method of any one of clauses 1-27, wherein the boron carbide particles are in a suspension.

Clause 29. The method of any one of clauses 1-28, wherein the boron carbide is associated with a solid support.

Clause 30. The method of clause 29, wherein the solid support is selected from the group consisting of a magnetic particle and a column.

Clause 31. The method of clause 29, wherein the solid support is used in a magnetic, centrifugation, or filtration format.

Clause 32. The method of any one of clauses 1-31, further comprising using or characterizing the isolated nucleic acid.

It is understood that the foregoing detailed description and accompanying examples are merely illustrative and are not to be taken as limitations upon the scope of the invention, which is defined solely by the appended claims and their equivalents.

Various changes and modifications to the disclosed embodiments will be apparent to those skilled in the art. Such changes and modifications, including without limitation those relating to the chemical structures, substituents, derivatives, intermediates, syntheses, compositions, formulations, or methods of use of the invention, may be made without departing from the spirit and scope thereof.

What is claimed is:

1. A method for isolating nucleic acids from a sample, the method comprising:
   (a) contacting the sample with a boron carbide composition under conditions sufficient to form a boron carbide-nucleic acid complex;
   (b) separating the complex from the sample; and
   (c) eluting the nucleic acids from the complex, thereby isolating the nucleic acids.

2. The method of claim 1, wherein the sample is prepared in the absence of an organic extraction.

3. The method of claim 2, wherein the organic extraction comprises phenol and chloroform.

4. The method of claim 3, wherein the phenol is an acid phenol.

5. The method of claim 1, further comprising contacting the sample with a chaotrope.

6. The method of claim 5, wherein the chaotrope is present in a lysis or binding buffer.

7. The method of claim 5, wherein the chaotrope is guanidine thiocyanate (GTC) or guanidine hydrochloride (GHCl).

8. The method of claim 1, wherein the boron carbide composition further comprises glass fibers.

9. The method of claim 1, wherein the boron carbide-nucleic acid complex is formed in the presence of an alcohol.

10. The method of claim 9, wherein the alcohol is isopropanol or ethanol.

11. The method of claim 1, wherein formation of the boron carbide-nucleic acid complex comprises selective binding of the nucleic acid to the boron carbide and wherein selective binding is dependent upon a concentration of an alcohol.

12. The method of claim 11, wherein the alcohol is isopropanol or ethanol.

13. The method of claim 12, wherein the nucleic acid is RNA and wherein the RNA selectively binds the boron carbide when the concentration of alcohol is from about 15% v/v to about 100% v/v.

14. The method of claim 13, wherein the RNA is large RNA and wherein the large RNA selectively binds the boron carbide when the concentration of isopropanol is from about 15% to about 20%.

15. The method of claim 13, wherein the RNA is large RNA and wherein the large RNA selectively binds the boron carbide when the concentration of ethanol is from about 20% v/v to about 35% v/v.

16. The method of claim 13, wherein the RNA is small RNA and wherein the small RNA selectively binds the boron carbide when the concentration of isopropanol is about 40% v/v to about 60% v/v.

17. The method of claim 13, wherein the RNA is small RNA and wherein the small RNA selectively binds the boron carbide when the concentration of ethanol is about 50% v/v to about 70% v/v.

18. The method of claim 14, wherein the RNA is long, noncoding RNA.

19. The method of claim 15, wherein the small RNA is selected from the group consisting of microRNA (miRNA), small interfering RNA (siRNA), piwi-interacting RNA (piRNA), small noncoding RNA, small nuclear RNA (snRNA), small nucleolar RNA (snoRNA), and transfer RNA (tRNA).

20. The method of claim 19, wherein the small RNA is miRNA.

21. The method of claim 1, wherein the nucleic acid is RNA.

22. The method of claim 21, wherein the RNA is small RNA.

23. The method of claim 21, wherein the RNA is microRNA (miRNA).

24. The method of claim 21, wherein the RNA comprises RNA molecules having a length of about 5 nucleotides to about 200 nucleotides.

25. The method of claim 24, wherein the RNA comprises RNA molecules having a length of about 10 nucleotides to about 100 nucleotides.

26. The method of claim 24, wherein the RNA comprises RNA molecules having a length of about 18 nucleotides to about 30 nucleotides.

27. The method of claim 1, wherein the boron carbide has a particle size of about 1 micron to about 20 microns.

28. The method of claim 27, wherein the boron carbide particles are in a suspension.

29. The method of claim 1, wherein the boron carbide is associated with a solid support.

30. The method of claim 29, wherein the solid support is selected from the group consisting of a magnetic particle and a column.

31. The method of claim 29, wherein the solid support is used in a magnetic, centrifugation, or filtration format.

32. The method of claim 1, further comprising using or characterizing the isolated nucleic acid.

* * * * *